US010604770B2

United States Patent
Saito et al.

(10) Patent No.: US 10,604,770 B2
(45) Date of Patent: Mar. 31, 2020

(54) METHOD FOR EXTRACTING DIFFERENTIATED CELLS

(71) Applicant: KYOTO UNIVERSITY, Kyoto (JP)

(72) Inventors: Hirohide Saito, Kyoto (JP); Kei Endo, Kyoto (JP); Shota Katayama, Kyoto (JP); Callum Parr, Kyoto (JP)

(73) Assignee: KYOTO UNIVERSITY, Kyoto (JP)

( * ) Notice: Subject to any disclaimer, the term of this patent is extended or adjusted under 35 U.S.C. 154(b) by 0 days.

(21) Appl. No.: 15/326,083

(22) PCT Filed: Jul. 16, 2015

(86) PCT No.: PCT/JP2015/070425
§ 371 (c)(1),
(2) Date: Aug. 9, 2017

(87) PCT Pub. No.: WO2016/010119
PCT Pub. Date: Jan. 21, 2016

(65) Prior Publication Data
US 2017/0342439 A1    Nov. 30, 2017

(30) Foreign Application Priority Data

Jul. 16, 2014  (JP) ................................ 2014-146070

(51) Int. Cl.
*C12N 15/85* (2006.01)
*C12N 5/0793* (2010.01)
*C12N 5/074* (2010.01)

(52) U.S. Cl.
CPC .......... *C12N 15/85* (2013.01); *C12N 5/0619* (2013.01); *C12N 5/0696* (2013.01); *C12N 2501/385* (2013.01); *C12N 2501/65* (2013.01); *C12N 2506/45* (2013.01); *C12N 2510/00* (2013.01); *C12N 2533/50* (2013.01)

(58) Field of Classification Search
CPC . C12N 15/85; C12N 5/0696; C12N 2310/141
See application file for complete search history.

(56) References Cited

U.S. PATENT DOCUMENTS

| 2009/0286242 A1* | 11/2009 | Hannon | C12Q 1/6883 435/6.12 |
| 2010/0317532 A1* | 12/2010 | Liu | C12N 15/1086 506/7 |
| 2010/0323356 A1* | 12/2010 | Inoue | C12N 15/111 435/6.14 |
| 2013/0150256 A1 | 6/2013 | Synnergren et al. | |
| 2014/0073687 A1* | 3/2014 | Chien | A01K 67/0276 514/44 R |

FOREIGN PATENT DOCUMENTS

| EP | 2202309 | 6/2010 | |
| JP | 2009-171861 A | 8/2009 | |
| JP | 2010-158171 A1 | 7/2010 | |
| WO | WO-2011154553 A2 * | 12/2011 | ........... C12N 15/113 |
| WO | WO 2013/188679 A1 | 12/2013 | |
| WO | WO 2015/105172 A1 | 7/2015 | |

OTHER PUBLICATIONS

Lipchina et al. Cell Cycle 11: 1517-1523 (Year: 2012).*
Supplementary European Search Report and Opinion, EP 15822080.6, dated Dec. 11, 2017.
Kamata M et al. Live cell monitoring of hiPSC generation and differentiation using differential expression of endogenous microRNAs. PLoS ONE. Jul. 2010; 5(7): e11834.
Subramanyam D et al. Multiple targets of miR-302 and mkR-372 promote reprogramming of human fibroblasts to induced pluripotent stem cells. Nat Biotechnol. May 2011; 29(5): 443-448.
Parr CJC et al. MicroRNA-302 switch to identify and eliminate undifferentiated human pluripotent stem cells. Scienctific Reports. Sep. 9, 2016; 6:32532.
Nakanishi H et al. Monitoring and visualizing microRNA dynamics during live cell differentiation using microRNA-responsive non-viral reporter vectors. Biomaterials. 2017; 12E: 121-135.
Miura K et al. Nat Biotechnol. Variation in the safety of induced pluripotent stem cell lines. Aug. 2009; 27(8): 743-745.
International Search Report, PCT/JP2015/070425, dated Sep. 8, 2015.
Diekmann U et al. MicroRNA target sites as genetic tools to enhance promoter-reporter specificity for the purification of pancreatic progenitor cells from differentiated embryonic stem cells, Stem Cell Rev. Aug. 2013; 9(5): 555-568.
Warren L et al. Highly efficient reprogramming to pluripotency and directed differentiation of human cells with synthetic modified mRNA. Cell Stem Cell, Nov. 5. 2010; 7(5): 618-630.
Miki K et al. Efficient detection and purification of cell populations using synthetic microRNA switches. Cell Stem Cell. Jun. 4, 2015: 16(6): 699-711.
Miki K et al. Efficient detection and purification of cells by syntheic microRNA switches. Regenerative Medicine. Feb. 1, 2015; 14(supp):188.
Sachdeva et al. "Tracking differentiating neural progenitors in pluripotent cultures using microRNA-regulated lentiviral vectors" PNAS, 107(25)11602-11607 (2010).
Examination Report corresponding to European Patent Application No. 15822080.6, dated Nov. 20, 2018, 6 pages.
Japanese Office Action corresponding to Japanese Patent Application No. 2016-534491, dated May 14, 2019, including English translation, 7 pages total.

* cited by examiner

Primary Examiner — Brian Whiteman
(74) Attorney, Agent, or Firm — Myers Bigel, P.A.

(57) ABSTRACT

A method for extracting differentiated cells from a cell population comprising undifferentiated cells after induction of the differentiation of pluripotent stem cells. A method for extracting differentiated cells from a cell population, comprising the following steps: (1) a step of introducing, into a cell population, mRNA comprising a marker gene operably linked to the target sequence of miRNA specifically expressed in pluripotent stem cells; and (2) a step of extracting cells in which the marker gene has been translated.

13 Claims, 9 Drawing Sheets

Specification includes a Sequence Listing.

A

B a

*Ff-hiPSC line 201B7 @d0* b c d a b c

*Repeat 1*

*Repeat 2, larger volume analyzed*

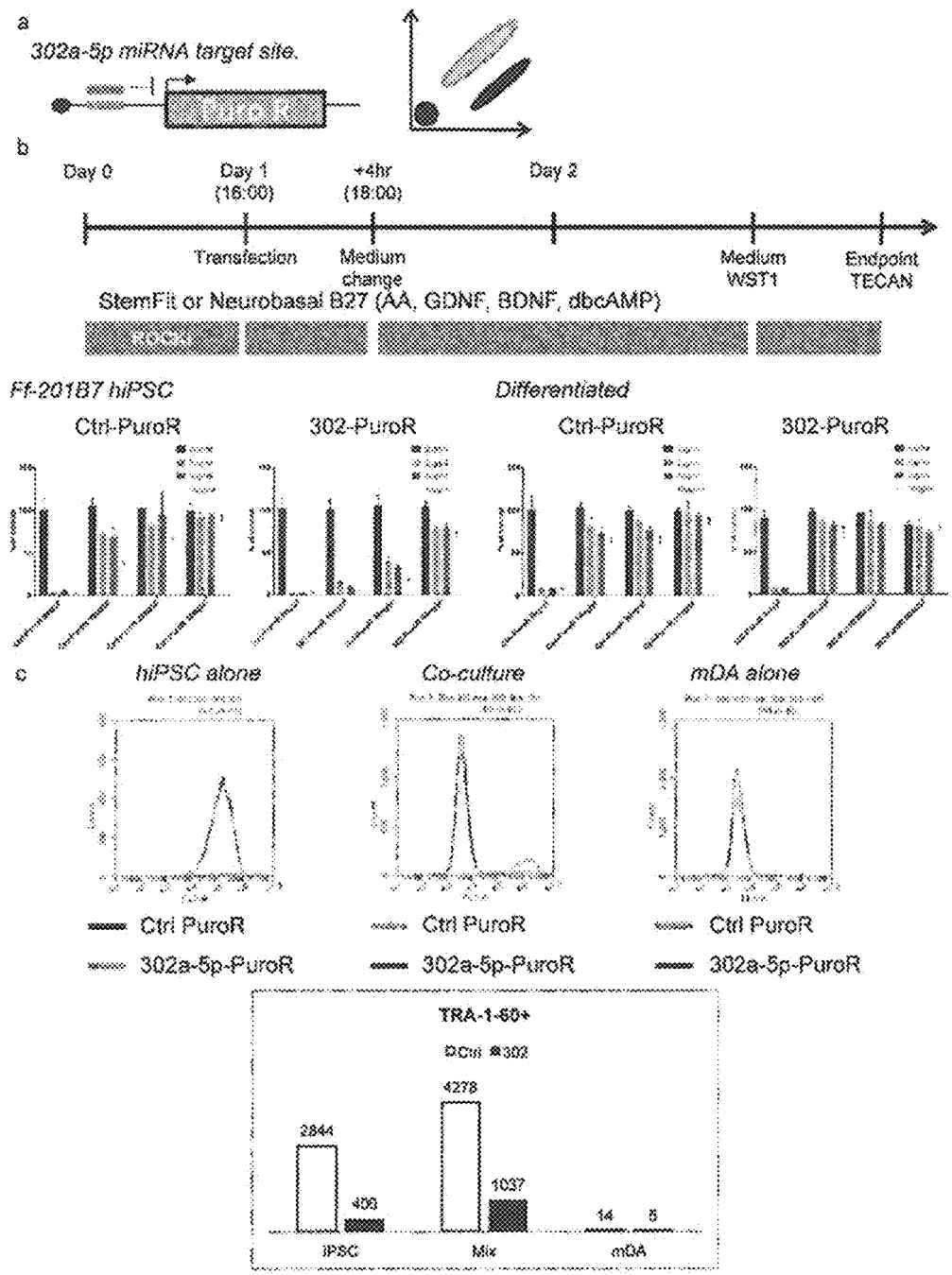

METHOD FOR EXTRACTING DIFFERENTIATED CELLS

RELATED APPLICATIONS

This application is a 35 U.S.C. § 371 national phase application of PCT Application PCT/JP2015/070425 filed Jul. 16, 2015, which claims priority to Japanese Application No. 2014-146070 filed Jul. 16, 2014, the disclosure of each of which is incorporated herein by reference in its entirety.

STATEMENT REGARDING ELECTRONIC FILING OF A SEQUENCE LISTING

A Sequence Listing in ASCII text format, submitted under 37 C.F.R. § 1.821, entitled 5576-331_ST25.txt, 19,014 bytes in size, generated on Jan. 12, 2017, and filed via EFS-Web, is provided in lieu of a paper copy. This Sequence Listing is hereby incorporated by reference into the specification for its disclosures.

TECHNICAL FIELD

The present invention relates to a method for extracting differentiated cells, using, as an indicator, miRNA specifically expressed in pluripotent stem cells.

Attention has been paid to cell therapy, in which pluripotent stem cells such as iPS cells or ES cells are induced to differentiate into desired cells, and the differentiated cells are then administered into a body. However, even after completion of the differentiation induction, undifferentiated cells are likely to remain, and thus, it has been pointed out that if a cell population comprising such undifferentiated cells is administered, it would cause canceration (Non Patent Literature 1).

Hence, a method for removing such remaining undifferentiated cells, using a cell surface marker highly expressed in pluripotent stem cells as an indicator, has been studied. However, it is not always the case that the cell surface marker highly expressed in pluripotent stem cells is not expressed in differentiated cells. Even if cells, in which the cell surface marker highly expressed in pluripotent stem cells is negative, are extracted, there are cases in which undifferentiated cells cannot be completely removed. Moreover, the type of such a cell surface marker is limited, and it is difficult to find a more specific marker.

CITATION LIST

Non Patent Literature

[Non Patent Literature 1] Miura K, et al., Nat Biotechnol. 2009 27:743-745

SUMMARY OF INVENTION

Technical Problem

It is desired to develop a method for extracting differentiated cells from a cell population comprising undifferentiated cells after induction of the differentiation of pluripotent stem cells.

Solution to Problem

The present inventors have found that miRNA specifically expressed in pluripotent stem cells is utilized, and that only differentiated cells can be extracted by using mRNA in which the expression of a marker gene is suppressed by the expression of the miRNA, thereby completing the present invention.

Specifically, the present invention has the following features:

[1] A method for extracting differentiated cells from a cell population after induction of the differentiation of pluripotent stem cells, comprising the following steps; (1) a step of introducing, into a cell population, mRNA comprising a marker gene operably linked to a target sequence of miRNA specifically expressed in pluripotent stem cells; and (2) a step of extracting cells in which the marker gene has been translated.
[2] The method according to [1], wherein the pluripotent stem, cells are human pluripotent stem cells.
[3] The method according to [2], wherein the miRNA specifically expressed in the human pluripotent stem cells is hsa-miR-302b, hsa-miR-302a, or hsa-miR-367.
[4] The method according to any one of [1] to [3], wherein the step of extracting is carried out using a flow cytometer.
[5] A differentiated cell extraction kit, which comprises mRNA comprising a marker gene operably linked to the target sequence of miRNA specifically expressed in pluripotent stem cells.
[6] The kit according to [5], wherein the pluripotent stem cells are human pluripotent stem cells.
[7] The kit according to [6], wherein the miRNA specifically expressed in the human pluripotent stem cells is hsa-miR-302b, hsa-miR-302a, or hsa-miR-367.

Advantageous Effects of Invention

According to the present invention, by utilizing mRNA having a marker gene operably linked to miRNA specific to pluripotent stem cells, differentiated cells can be selectively extracted. Since the method according to the present invention can be achieved by selecting cells, to which the marker has turned positive, the present method is particularly advantageous in that it is not influenced by the introduction efficiency of the mRNA. In addition, the method of the present invention can be carried out by introducing mRNA into cells, and this mRNA is decomposed in a half-life of approximately 1 day and it is then promptly discharged from the cells. Accordingly, the present method does not cause problems, such as damage given to the genome as a result of viral infection in cells or the remaining of DNA. Moreover, the present method is also advantageous in that it can select differentiated cells by a simple detection method using a cytometer, or drug selection by introduction of a drug resistance gene.

BRIEF DESCRIPTION OF DRAWINGS

FIG. 8a shows, from left, representative dot plots of 302a-5p-responsive mRNA-introduced Ff-201B7 cells on day 0, day 5, day 7, and day 14. On day 0, the blue dot plot (the lower dot group in the chart) shows high translational suppression by 302a-5p-responsive mRNA, and it is found that, as differentiation progresses, the overlapping of dot groups is increased, and thus, that the translation-suppressing effect is decreased. FIG. 8b shows the distribution of 302a-5p or 367-3p-responsive cells (blue region) and the distribution of 302a-5p- or 367-3p-non-responsive cells (red region) during differentiation of Ff-human iPS cells. FIG. 8c shows a time-lapse change occurring during differentiation in the percentage of cells responding to 302a-5p-responsive mRNA (left view), and a time-lapse change occurring during differentiation in the percentage of cells responding to 367-3p responsive mRNA (right view). The error bar indicates a standard error when trials were repeated three times.

FIG. 11a shows a scheme of removing the remaining iPS cells by addition of puromycin. FIG. 11b shows an experiment timeline of a single culture system (upper view), and the results of a cytotoxicity assay (lower view, graphs). The left two panels show the results obtained by introducing PuroR mRNA (Ctrl-PuroR) or 302a-5p responsive puroR mRNA (302-PuroR) into Ff-201B7 human iPS cells, and then performing a cytotoxicity assay by addition of puromycin, and the right two panels the results obtained by introducing PuroR mRNA (Ctrl-PuroR) or 302a-5p-responsive puroR mRNA (302-PuroR) into mDA cells induced from Ff-201B7 human iPS cells, and then performing a cytotoxicity assay by addition of puromycin. FIG. 11c shows: the results obtained by introducing PuroR mRNA (Ctrl-PuroR) or 302a-5p-responsive puroR mRNA into human iPS cells (upper left panel), mixed cells of human iPS cells and mDA cells (upper central panel), and mDA cells (upper right panel), then adding puromycin to the cells, then staining the cells with an. Alexa-488-conjugated anti-human TRA-1-60 antibody (BD laboratories), and then measuring the cells with BD Accuri; and a bar graph showing the absolute number of TRA-1-60-positive cells under different conditions (lower panel).

DESCRIPTION OF EMBODIMENTS

Figure 1:
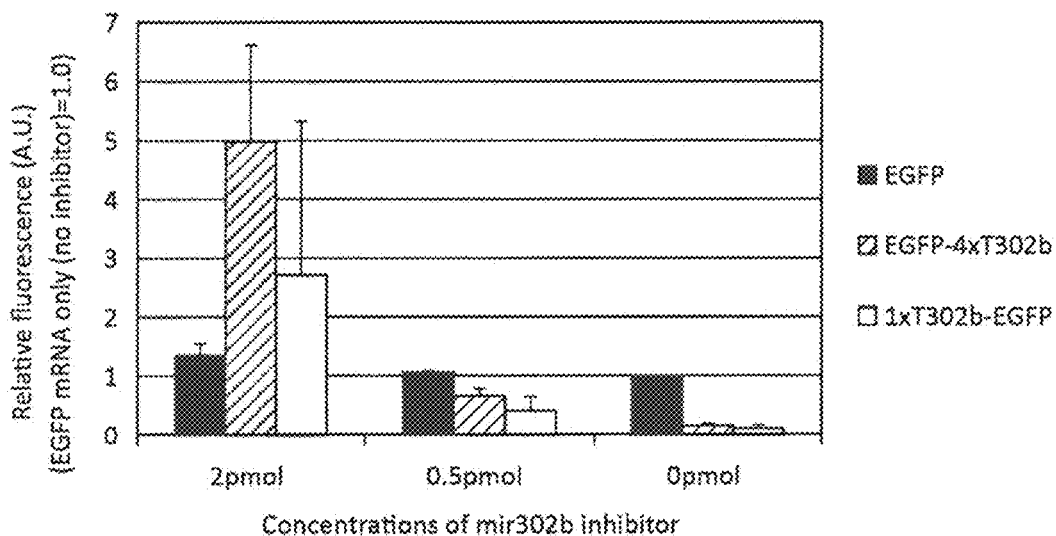
FIG. 1 shows the results obtained by introducing EGFP, 1xT302b-EGFP and EGFP-4xT302b into iPS cells, then culturing the iPS cells in a medium, to which a mirVana miRNA inhibitor had been added in different concentrations, and then measuring the fluorescence intensity of EGFP in the cultured iPS cells. In the figure, the error bar indicates an average±standard deviation (n=3).

Hereinafter, the present invention will be described in detail in the following embodiments. However, these embodiments are not intended to limit the scope of the present invention.

According to one embodiment, the present invention relates to a method for extracting differentiated cells from a cell population in which undifferentiated cells may be present after induction of the differentiation of pluripotent stem cells, wherein the method includes the following steps: (1) a step of introducing, into a cell population, mRNA comprising a marker gene operably linked to the target sequence of miRNA specifically expressed in pluripotent stem cells; and (2) a step of extracting cells in which the marker gene has been translated.

In the present invention, the pluripotent stem cells mean stem cells having pluripotency by which the cells are capable of differentiating into ail cells existing in a living body, and also having proliferative capacity. Examples of such pluripotent stem cells include embryonic stem (ES) cells (J. A. Thomson et al. (1998), Science 282:1145-1147; J. A. Thomson et al. (1995), Proc. Natl. Acad. Sci. USA, 92: 7844-7848; J. A. Thomson et al. (1996), Biol. Reprod., 55: 254-259:1. J. A. Thomson and V. S. Marshall (1998), Curr. Top. Dev. Biol., 38: 133-165), embryonic stem cells derived from cloned embryos obtained by nuclear transplantation (ntES) (T. Wakayama et at (2001), Science, 292:740-743; S. Wakayama et al (2005), Biol. Reprod., 72: 932-936; J. Byrne et al. (2007), Nature, 450: 497-502), spermatogonial stem cells ("GS cells") (M. Kanatsu-Shinohara et al. (2003) Biol. Reprod., 69: 612-616; K. Shinohara et al. (2004), Cell 119: 1001-1012), embryonic germ cells ("EG cells") (Y. Matsui et al. (1992), Cell, 70: 841-847; J. L. Resnick et al. (1992), Nature, 359: 550-551), induced pluripotent stem (iPS) cells (K. Takahashi and S. Yamanaka (2006) Cell, 126: 663-676; K. Takahashi et al. (2007), Cell, 131: 861-872; J. Yu et al. (2007), Science, 318:1917-1920; Nakagawa, M. et al., Nat. Biotechnol. 26:101-106 (2008); WO2007/069666), cultured fibroblast- or bone marrow stem cell-derived pluripotent cells (Muse cells) (WO2011/007900). More preferably, the pluripotent stem cells are human pluripotent stem cells.

In the present invention, induction of differentiation does not only mean differentiation of cells into specific tissue cells or progenitor cells thereof, but also means differentiation of cells into a cell population comprising many types of cells such as endodermal cells, mesodermal cells and ectodermal cells. In addition, examples of tissues as the target of the present invention include, but are not limited to, skin, blood vessel, cornea, kidney, heart, liver, umbilical cord, bowel, nerve, lung, placenta, pancreas, brain, cartilage, peripheral limbs, and retina. As for this differentiation induction method, a method well known to a person skilled in the art can be applied, and the method is not particularly limited, Regarding differentiation induction of neural stem cells. Japanese Patent Laid-Open No. 2002-291469 can be referred to, regarding differentiation induction of pancreatic stem-like cells, Japanese Patent Laid-Open No. 2004-121165 can be referred to, and regarding differentiation induction of hematopoietic cells, Japanese translation of PCT international application No. 2003-505006, etc. can be referred to. Other than these, an example of a differentiation induction method involving the formation of an embryoid body is described in Japanese translation of PCT international application No. 2003-523766.

In the present description, the cell population after induction of the differentiation of pluripotent stem cells means a cell population obtained after carrying out a method for induction of differentiation on the above-described pluripotent stem cells. There may be a case in which the cell population after induction of the differentiation includes undifferentiated cells. The method of the present invention can also be applied, even if whether or not the cell population includes undifferentiated cells is unknown. Preferably, the cell population after induction of the differentiation of pluripotent stem cells is a cell population in which undifferentiated cells are also present after induction of the differentiation of pluripotent stem cells.

In the present invention, miRNA is also referred to as "micro-RNA," and this is RNA having a length of approximately 18 to 25 nucleotides that is present in a cell. The miRNA means either one strand of double-stranded RNA, which is generated by cleaving with Dicer, pre-miRNA that has been generated by partially cleaving pri-mRNA as single-stranded RNA transcribed from DNA, with an intranuclear enzyme called Drosha. The number of nucleotides in the miRNA is, for example, 18 to 25, preferably 20 to 25, and more preferably 21 to 23. Database, in which information regarding approximately 1,000 miRNAs is stored, can be utilized (e.g., miRBase, microrna.sanger.ac.uk/sequences/index.shtml). A person skilled in the art can extract any given miRNA information from this database, and it is possible to easily extract miRNA specifically expressed in pluripotent stem cells. For example, by applying means available to a person skilled in the art, such as miRNA microarray or real-time PCR, a difference in the expression of miRNA can be confirmed between pluripotent stem cells and cells after induction of the differentiation of the pluripotent stem cells. Thereby, it is possible to easily specify miRNA that is expressed in pluripotent stem cells at a higher level than in cells after induction of the differentiation, to be miRNA specifically expressed in pluripotent stem cells. It is to be noted that miRNA expressed in pluripotent stem cells means miRNA that is in a state in which either one strand of the above-described double-stranded RNA cleaved with Dicer interacts with a plurality of predetermined proteins to form an RNA-induced silencing complex (RISC) in pluripotent stem cells.

In the present invention, the miRNA specifically expressed in pluripotent stem cells is not particularly limited, as long as it is miRNA that has been known to be specifically expressed in pluripotent stem cells according to publications and the like. Examples of such miRNA include either one strand selected from hsa-mir-302a, hsa-mir-302b, hsa-mir-302c, hsa-mir-302d, hsa-mir-367, hsa-5201, hsa-mir92b, hsa-mir-106a, hsa-mir-18b, hsa-mir-20b, hsa-mir-19b-2, hsa-mir-92a-2, hsa-mir-363, hsa-mir-20a, hsa-mir-17, hsa-mir-18a, hsa-mir-19a, hsa-mir-19b-1, hsa-mir373, hsa-mir-330, hsa-mir-520c, hsa-mir-182, hsa-mir-183, hsa-mir-96, hsa-mir-92a-1, hsa-mir-92a-2, hsa-mir-141, hsa-mir-200c, hsa-mir-27a, hsa-mir-7-1, hsa-mir-7-2, hsa-mir-7-3, hsa-mir-374a, hsa-mir-106b, hsa-mir-93, hsa-mir-25, hsa-mir-584, hsa-mir-374b, hsa-mir-21, hsa-mir-212, hsa-mir-371a, hsa-mir-371b, hsa-mir-372, hsa-mir-200b, hsa-mir-200a, and hsa-mir-429. Other than these examples, miRNA appropriately selected from the miRNAs described in Tobias S. Greve, et al, Annu. Rev. Cell Dev. Biol. 2013. 29: 213-239 can be used. Preferred examples of the miRNA include hsa-mir-302a, hsa-mir-302b, and hsa-mir-367, and more preferred examples include hsa-miR-302b-3p, hsa-mir-302a-5p, and hsa-mir-367-3p.

In the present invention, the target sequence of the miRNA specifically expressed in pluripotent stem cells means a sequence capable of specifically binding to the miRNA. The miRNA target sequence is preferably a sequence complementary to, for example, the miRNA specifically, expressed in pluripotent stem cells. Alternatively, as long as the miRNA target sequence is recognizable by miRNA, it may also have a mismatch with the completely complementary sequence. The mismatch with the sequence completely complementary to the miRNA may be generally a mismatch, which is recognizable by the miRNA in a desired cell, and it is considered that there may be a mismatch of approximately 40% to 50% with regard to the original function of the cell, in a living body. Such a mismatch is not particularly limited, and it is, for example, a mismatch of 1%, 5%, 10%, 20%, 30% or 40% of 1 nucleotide, 2 nucleotides, 3 nucleotides, 4 nucleotides, 5 nucleotides, 6 nucleotides, 7 nucleotides, 8 nucleotides, 9 nucleotides, 10 nucleotides or the entire recognition sequence. In addition, in particular, as with the miRNA target sequence of mRNA included in a cell, the target, sequence may include a large number of mismatches particularly in a portion other than a seed region, namely, in a region on the 5'-terminal side in the target sequence, which corresponds to approximately 16 nucleotides on the 3-terminal side of miRNA. The seed region may not include such mismatches, or may include a mismatch of 1 nucleotide, 2 nucleotides or 3 nucleotides.

The marker gene is an RNA sequence encoding any given marker protein, which is translated in a cell, functions as a marker, and enables extraction of differentiated cells, and this marker gene can also be referred to as a sequence corresponding to a marker protein. Examples of the protein, which is translated in a cell and is able to function as a marker, may include, but are not limited to, a fluorescent protein, a photoprotein, a color protein, a protein which can be visualized and can be quantified by supporting fluorescence, luminescence or color development, a membrane-localized protein, and a drug resistance protein.

Examples of the fluorescent protein include: blue fluorescent proteins such as Sirius or EBFP; cyan fluorescent proteins such as mTurquoise, TagCFP, AmCyan, mTFP1, MidoriishiCyan, or CFP; green fluorescent proteins such as TurboGFP, AcGFP, TagGFP, Azami-Green (e.g. hmAG1), ZsGreen, EmGFP, EGFP, GFP2, or HyPer; yellow fluorescent proteins such as TagYFP, EYFP, Venus, YFP, PhiYFP, PhiYFP-m, TurboYFP, ZsYellow, or mBanana; orange fluorescent proteins such as KusabiraOrange (e.g. hmKO2) or mOrange; red fluorescent proteins such as TurboRFP, DsRed-Express, DsRed2, TagRFP, DsRed-Monomer, AsRed2, or mStrawberry; and near infrared-fluorescent proteins such as TurboFP602, mRFP1, JRed, KillerRed, mCherry, HcRed, KeimaRed (e.g. hdKeimaRed), mRasberry, or mPlum, but examples of the fluorescent protein are not limited thereto.

An example of the luminescent protein is aequorin, but examples are not limited thereto. In addition, examples of the protein supporting fluorescence, luminescence or color development include enzymes decomposing fluorescence, luminescence or color development precursors, such as luciferase, phosphatase, peroxidase, or β lactamase, but examples of this protein are not limited thereto. In the present invention, when the substance supporting fluorescence, luminescence or color development is used as a marker, extraction of differentiated cells can be carried out by allowing the cells to come into contact with a corresponding precursor, or by introducing such a corresponding precursor into the cells.

The membrane-localized protein is not particularly limited, as long as it is a membrane-localized protein that, is not endogenously expressed in pluripotent stem cells. Examples of such, a membrane-localized protein include P-gp, MRP1, MRP2 (cMOAT), MRP3, MRP4, MRP5, MRP6, MDR2, and MDR3 proteins. In the present invention, since a membrane-localized protein translated from the introduced mRNA is used as an indicator, a membrane-localized protein that is not endogenously expressed in target differentiated cells is more preferable. Examples of the drug resistance protein include antibiotic resistance proteins such as a kanamycin resistance protein, an ampicillin resistance protein, a puromycin resistance protein, a blasticidin resistance protein, a gentamicin resistance protein, a kanamycin resistance protein, a tetracycline resistance protein, and a chloramphenicol resistance protein, but the examples are not limited thereto.

The mRNA to be used for introduction into a cell population by the method of the present invention includes a marker gene operably linked to the target sequence of the miRNA specifically expressed in pluripotent stem cells, in the explanation of the present invention, such mRNA is also referred to as "miRNA-responsive reporter mRNA." in the present invention, the phrase "a marker gene is operably linked to the target sequence of the miRNA" means that at least one miRNA target sequence is included in the 5' UTR and 3' UTR of an open reading frame encoding the marker gene (including an initiation codon), and/or in the open reading frame. The mRNA preferably includes, in the direction from the 5'-terminus to the 3-terminus, a Cap structure (7-methylguanosine 5'-phosphate), an open reading frame encoding the marker gene, and poly(A) tail, and also includes, in the 5' UTR, in the 3' UTR, and/or in the open reading frame, at least one miRNA target sequence. The position of the miRNA target sequence in the mRNA may be either in 5' UTR or in 3' UTR, or may also be in the open reading frame (on the 3'-terminal side of the initiation codon). Otherwise, the mRNA may include miRNA target sequences in all of these positions. Accordingly, the number of miRNA target sequences may be 1, 2, 3, 4, 5, 6, 7, 8, or more.

Preferably, one miRNA target sequence is present in the 5' UTR. This is because it can achieve efficient translational suppression. At this time, the number of nucleotides and the type of nucleotides between the Cap structure and the miRNA target sequence may be freely determined, as long as they do not include AUG serving as an initiation codon and do not constitute a stem structure or a steric structure. For instance, the Cap structure and the miRNA target sequence can be designed, such that the number of nucleotides between the Cap structure and the miRNA target sequence can be 0 to 50 nucleotides, and preferably 10 to 30 nucleotides. Moreover, the number of nucleotides and the type of nucleotides between the miRNA target sequence and the initiation codon may be freely determined, as long as they do not constitute a stem structure or a steric structure. The miRNA target sequence and the initiation codon can be designed, such that the number of nucleotides between the miRNA target sequence and the initiation codon is 0 to 50 nucleotides, and preferably 10 to 30 nucleotides. It has been confirmed that translational suppression can be achieved, even if four miRNA target sequences are present in the 3' UTR.

The miRNA-responsive reporter mRNA preferably includes modified nucleotides such as pseudo uridine and 5-methylcytidine, instead of ordinary uridine and cytidine. This is because of reduction in cytotoxicity. Such modified nucleotides can be positioned independently or as the whole or a part of the mRNA, in both cases of uridine and cytidine. In the case of being included as a part, the nucleotides can be positioned randomly at any given ratio.

After the sequence of the miRNA-responsive reporter mRNA has been determined as described above, a person skilled in the art is able to synthesize the miRNA-responsive reporter mRNA according to any given known genetic engineering method. In particular, the miRNA-responsive reporter mRNA can be obtained according to an in vitro synthesis method, using template DNA comprising a promoter sequence as a template.

In one embodiment of the present invention, there is a case in which only one type of miRNA-responsive reporter mRNA is used, or there is also a case in which two or more types of, for example, three types, four types, five types, six types, seven types, or eight types or more of miRNA-responsive reporter mRNAs are used. When differentiated cells are extracted using, as indicators, two or more types of different miRNAs specifically expressed in pluripotent stem cells, it is preferable to use two or more types of miRNA-responsive reporter mRNAs corresponding to the two or more types of miRNAs. For example, in the case of using two or more types of miRNA-responsive reporter mRNAs, it is desirable that the miRNA-responsive reporter mRNAs be different from one another, in terms of the miRNA target sequence and the marker gene. In addition, in the case of using two or more types of miRNA-responsive reporter mRNAs, the number of miRNA target sequences included in the miRNA-responsive reporter mRNA, the distance of the miRNA target sequence from the 5'-terminus, and other structural characteristics of the miRNA-responsive reporter mRNA may be different among individual miRNA-responsive reporter mRNAs.

In one embodiment of the present invention, in the step of introducing miRNA-responsive reporter mRNA into a cell population (hereinafter referred to as an "introduction step"), one or more types of miRNA-responsive reporter mRNAs are directly introduced into cells included in a cell population, by applying a lipofection method, a liposome method, an electroporation method, a calcium phosphate co-precipitation method, a DEAE dextran method, a micro-injection method, a gene gun method, etc. In the case of introduction of two or more different types of miRNA-responsive reporter mRNAs, a plurality of mRNAs are preferably co-introduced into a cell population. This is because the ratio of the activities of marker proteins expressed from the thus co-introduced two or more mRNAs is constant in a cell population. At this time, the amount of miRNA-responsive reporter mRNA introduced may be different depending on the type of a cell population into which the mRNA is to be introduced, the type of the introduced mRNA, a method of introducing, the mRNA, and the types of introduction reagents. In order to achieve a desired translation level, a person skilled in the art can appropriately select these conditions.

In one embodiment of the present invention, when the miRNA-responsive reporter mRNA of the present invention is introduced into a cell population comprising undifferentiated cells after induction of the differentiation of pluripotent stem cells, the translation level of a marker gene encoded by the miRNA-responsive reporter mRNA is not suppressed, since certain miRNA is not present in the form of RISC in differentiated cells. That is to say, the translation of the marker gene is carried out only in the differentiated cells. Accordingly, in one embodiment of the present invention, by extracting cells in which the marker gene has been translated, it becomes possible to selectively extract only differentiated cells from a cell population also comprising undifferentiated cells after induction of the differentiation of pluripotent stem cells.

A step of extracting the cells in which the marker gene has been translated is carried out (hereinafter, referred, to as an "extraction step"). In the extraction step, the above described cells in which the marker gene has been translated and the expression of the marker protein has been confirmed, are extracted as differentiated cells. That is, this extraction step can be carried out by comparing a cell population into which mRNA comprising a marker gene operably linked to the target sequence of miRNA has been introduced, with a cell population into which such mRNA comprising a marker gene operably linked to the target sequence of miRNA has not been introduced, and then by extracting cells in which the marker protein has been expressed, from the cell population into which the mRNA comprising a marker gene operably linked to the target sequence of miRNA has been introduced.

Specifically, the extraction step can be carried out by detecting signals from the marker protein, using a certain detection apparatus. For detection of signals from the marker protein, signals may be digitized and quantified, or only the presence or absence of signals may be detected. Examples of the detection apparatus include a flow cytometer, an imaging cytometer, a fluorescence microscope, a luminescence microscope, and a CCD camera, but examples are not limited thereto. As such a detection apparatus, a person skilled in the art can use a suitable apparatus, depending on a marker protein. For instance, when the marker protein is a fluorescent protein or a luminescent protein, it is possible to confirm the presence or absence of the expression of the marker protein and/or to quantify the marker protein, using a detection apparatus such as a flow cytometer, an imaging cytometer, a fluorescence microscope or a CCD camera. When the marker protein is a protein supporting fluorescence, luminescence or color development, it is possible to confirm the presence or absence of the expression of the marker protein or to quantify the marker protein, using a detection apparatus such as a luminescence microscope, a CCD camera or a luminometer. When the marker protein is a membrane localization protein, it is possible to confirm the presence or absence of the expression of the marker protein and/or to quantify the marker protein, using a detection reagent specific, to a cell surface protein such as an antibody, and the above-described detection apparatus. Moreover, it is also possible to apply a method of isolating cells without undergoing a process of quantifying the marker protein, such as a magnetic cell separation device (MACS). When the marker protein is a drug resistance protein, a method, which includes detecting the expression of the marker protein by administration of a drug and then isolating living cells, can be applied.

Prior to application of the method of the present invention, it is also possible to carry out an optional step of co-introducing control mRNA as well as miRNA-responsive reporter mRNA into undifferentiated cells and/or differentiated cells, and then confirming the translation efficiency of the miRNA-responsive reporter mRNA in the cells. By confirming and calculating the translation efficiency, whether the mRNA has been introduced into target cells and translation has been suppressed by the expression of the miRNA, or whether the mRNA has been introduced into the cells at a low level, can be comparatively studied. By carrying out such comparative studies, the mRNA to be used in the present invention can be selected, as appropriate. The control mRNA means mRNA, which does not have a miRNA target site and encodes a marker gene that is different from the marker gene encoded by the miRNA-responsive reporter mRNA. The control mRNA expresses a marker protein, regardless of the expression of miRNA. This is because, since the control mRNA does not have a miRNA target sequence, its translation is not regulated depending on the expression level of miRNA, even if it is introduced into cells.

The present invention further relates to a differentiated cell extraction kit, which includes mRNA comprising a marker gene operably linked to the target sequence of the aforementioned miRNA specifically expressed in pluripotent stem cells. The kit of the present invention may further include control mRNA. In addition, the kit of the present invention may also include discriminant analysis means, for example, papers or instructions in which the procedures for extracting differentiated cells are described, a program for allowing a computer to execute the procedures for extracting differentiated cells, a list of the programs, a computer-readable recording medium, in which the programs are recorded (e.g., a flexible disk, an optical disk, CD-ROM, CD-R, CD-RW, etc.), and a device or system for carrying out the extraction of differentiated cells (a computer, etc.).

EXAMPLES

Hereinafter, the present invention will be described more in detail in the following examples. However, these examples are not intended to limit the scope of the present invention.

Example 1

[Designing of miR-302b-Responsive Reporter mRNA]

EGFP mRNA (SEQ ID NO: 1), which encodes the fluorescence reporter gene EGFP and includes the five prime untranslated region. (5' UTR) and the three prime untranslated region (3' UTR) of α globin, was modified, and miR-302b-responsive reporter mRNA (1xT302b-EGFP) (SEQ ID NO: 2) comprising one copy of the target sequence of miR-302b in the 5' UTR and miR-302b-responsive reporter mRNA (EGFP-4xT302b) (SEQ ID NO: 3) comprising 4 copies of the target sequence of miR-302b in the 3' UTR were each designed. Moreover, mCherry mRNA (SEQ ID NO: 4) comprising the 51 UTR and 3' UTR of α globin, which was used as a control, was also designed. These gene sequences are shown below.

```
Gene sequence of EGFP-mRNA
                                         (SEQ ID NO: 1)
GGGCGAAUUAAGAGAGAAAAGAAGAGUAAGAAGAAAUAUAAGACACCGGU

CGCCACCAUGGGAUCCGUGAGCAAGGGCGAGGAGCUGUUCACCGGGGUGG

UGCCCAUCCUGGUCGAGCUGGACGGCGACGUAAACGGCCACAAGUUCAGC

GUGUCCGGCGAGGGCGAGGGCGAUGCCAGCUACGGCAAGCUGACCCUGAA

GUUCAUCUGCACCACCGGCAAGCUGCCCGUGCCCUGGCCCACCCUCGUGA

CCACCCUGACCUACGGCGUGCAGUGCUUCAGCCGCUACCCCGACCACAUG

AAGCAGCACGACUUCUUCAAGUCCGCCAUGCCCGAAGGCUACGUCCAGGA
```

```
-continued
GCGCACCAUCUUCUUCAAGGACGACGGCAACUACAAGACCCGCGCCGAGG

UGAAGUUCGAGGGCGACACCCUGGUGAACCGCAUCGAGCUGAAGGGCAUC

GACUUCAAGGAGGACGGCAACAUCCUGGGGCACAAGCUGGAGUACAACUA

CAACAGCCACAACGUCUAUAUCAUGGCCGACAAGCAGAAGAACGGCAUCA

AGGUGAACUUCAAGAUCCGCCACAACAUCGAGGACGGCAGCGUGCAGCUC

GCCGACCACUACCAGCAGAACACCCCCAUCGGCGACGGCCCCGUGCUGCU

GCCCGACAACCACUACCUGAGCACCCAGUCCGCCCUGAGCAAAGACCCCA

ACGAGAAGCGCGAUCACAUGGUCCUGCUGGAGUUCGUGADDGCCGCCGGG

AUCACUCUCGGCAUGGACGAGCUGUACAAGAGAUCUCAUAUGCAUCUCGA

GUGAUAGUCUAGACCUUCUGCGGGGCUUGCCUUCUGGCCAUGCCCUUCUU

CUCUCCCUUGCACCUGUACCUCUUGGUCUUUGAAUAAAGCCUGAGUAGGA

AAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAA

AAAAAAAAAAAAAAAAAAA
```

The underlined portion indicates 5' UTR or 3' UTR.

```
Gene sequence of 1xT302b-EGFP
                                         (SEQ ID NO: 2)
GGUCAGAUCCGCUAGGAUCctactaaaacatggaagcacttaCACCGGUC

GCCACCAUGGAUCCGUGAGCAAGGGCGAGGAGCUGUUCACCGGGGUGGUG

CCCAUCCUGGUCGAGCUGGACGGCGACGUAAACGGCCACAAGUUCAGCGU

GUCCGGCGAGGGCGAGGGCGAUGCCACCUACGGCAAGCUGACCCUGAAGU

UCAUCUGCACCACCGGCAAGCUGCCCGUGCCCUGGCCCACCCUCGUGACC

ACCCUGACCUACGGCGUGCAGUGCUUCAGCCGCUACCCCGACCACAUGAA

GCAGCACGACUUCUUCAAGUCCGCCAUGCCCGAAGGCUACGCCCAGGAGC

GCACCAUCUUCUUCAAGGACGACGGCAACUACAAGACCCGCGCCGAGGUG

AAGUUCGAGGGCGACACCCUGGUGAACCGCAUCGAGCUGAAGGGCAUCGA

CUUCAAGGAGGACGGCAACAUCCUGGGGCACAAGCUGGAGUACAACUACA

ACAGCCACAACGUCUAUAUCAUGGCCGACAAGCAGAAGAACGGCAUCAAG

GUGAACUUCAAGAUCCGCCACAACAUCGAGGACGGCAGCGUGCAGCUCGC

CGACCACUACCAGCAGAACACCCCCAUCGGCGACGCCCCGUGCUGCUGC

CCGACAACCACUACCUGAGCACCCAGUCCGCCCUGAGCAAAGACCCCAAC

GAGAAGCGCGAUCACAUGGUCCUGCUGGAGUUCGUGACCGCCGCCGGGAU

CACUCUCGGCAUGGACGAGGCUGUACAAGAGAUCUCAUAUGCAUCUCGAG

UGAUAGUCUAGACCUUCUGCGGGGCUUGCCUUCUGGCCAUGCCCUUCUUC

UCUCCCUUGCACCUGUACCUCUUGGUCUUUGAAUAAAGCCUGAGUAGGAA

AAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAA

AAAAAAAAAAAAAAAAAA
```

The underlined portion indicates 5' UTR or 3' UTR, and the lowercase letters indicate one copy of the miR-302b target sequence.

Gene sequence of EGFP-4xT302b
(SEQ ID NO: 3)

GGGCGAAUUAAGAGAGAAAAGAAGAGUAAGAAGAAAUAUAAGACACCGGU

CGCCACCAUGGGAUCCGUGAGCAAGGGCGAGGAGCUGUUCACCGGGGUGG

UGCCCAUCCUGGUCGAGCUGGACGGCGACGUAAACGGCCACAAGUUCAGC

GUGUCCGGCGAGGGCGAGGGCGAUGCCACCUACGGCAAGCUGACCCUGAA

GUUCAUCUGCACCACCGGCAAGCUGCCCGUGCCCUGGCCCACCCUCGUGA

CCACCCUGACCUACGGCGUGCAGUGCUUCAGCCGCUACCCCGACCACAUG

AAGCAGCACGACUUCUUCAAGUCCGCCAUGCCCGAAGGCUACGUCCAGGA

GCGCACCAUCUUCUUCAAGGACGACGGCAACUACAAGACCCGCGCCGAGG

UGAAGUUCGAGGGCGACACCCUGGUGAACCGCAUCGAGCUGAAGGGCAUC

GACUUCAAGGAGGACGGCAACAUCCUGGGGCACAAGCUGGAGUACAACUA

CAACAGCCACAACGUCUAUAUCAUGGCCGACAAGCAGAAGAACGGCAUCA

AGGUGAACUUCAAGAUCCGCCACAACAUCGAGGACGGCAGCGUGCAGCUC

GCCGACCACUACCAGCAGAACACCCCCAUCGGCGACGGCCCCGUGCUGCU

GCCCGACAACCACUACCUGAGCACCCAGUCCGCCCUGAGCAAAGACCCCA

ACGAGAAGCGCGAUCACAUGGUCCUGCUGGAGUUCGUGACCGCCGCCGGG

AUCACUCUCGGCAUGGACGAGCUGUACAAGAGAUCUCAUAUGCAUCUCGA

GUGAUAGUCUAGACCUUCUGCGGGCcuacuaaaacauccaagcacuuac uacuaaaacauggaagcacuuacuacuaaaacauggaagcacuuacuacu aaaacauggaagcauuaUGAAUAAAGCCUGAGUAGGAAAAAAAAAAAAA

AAAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAA

AAAAAA

The underlined portion indicates 5' UUR or 3' UTR, and the lowercase letters indicate 4 copies of the miR-302b target sequence.

Gene sequence of mCherry-mRNA
(SEQ ID NO: 4)

GGGCGAAUUAAGAGAGAAAAGAAGAGUAAGAAGAAAUAUAAGACACCGGU

CGCCACCAUGGUGAGCAAGGGCGAGGAGGAUAACAUGGCCAUCAUCAAGG

AGUUCAUGCGCUUCAAGGUGCACAUGGAGGGCUCCGUGAACGGCCACGAG

UUCGAGAUCGAGGGCGAGGGCGAGGGCCGCCCCUACGAGGGCACCCAGAC

CGCCAAGCUGAAGGUGACCAAGGGUGGCCCCCUGCCCUUCGCCUGGGACA

CAUCCUGUCCCCUCAGUUCAUGUACGGCUCCAAGGCCUACGUGAAGCACC

CCGCCGACAUCCCCGACUACUUGAAGCUGUCCUUCCCCGAGGGCUUCAAG

UGGGAGCGCGUGAUGAACUUCGAGGACGGCGGCGUGGUGACCGUGACCCA

GGACUCCUCCCUGCAGGACGGCGAGUUCAUCUACAAGGUGAAGCUGCGCG

GCACCAACUUCCCCUCCGACGGCCCCGUAAUGCAGAAGAAGACCAUGGGC

UGGGAGGCCUCCUCCGAGCGGAUGUACCCCGAGGACGGCGCCCUGAAGGG

CGAGAUCAAGCAGAGGCUGAAGCUGAAGGACGGCGGCCACUACGACGCUG

AGGUCAAGACCACCUACAAGGCCAAGAAGCCCGUGCAGCUGCCCGGCGCC

UACAACGUCAACAUCAAGUUGGACAUCACCUCCCACAACGAGGACUACAC

CAUCGUGGAACAGUACGAACGCGCCGAGGGCCGCCACUCCACCGGCGGCA

UGGACGAGCUGUACAAGUAAAUCUAGACCUUCUGCGGGCUUGCUUCUGGC

CAUGCCCUUCUUCUCUCCCUUGCACCUGUACCUCUUGGUCUUUGAAUAAA

GCCUGAGUAGGAAAAAAAAAAAAAAAAAAAAAAAAAAAAAAAAAAAAAA

AAAAAAAAAAAAAAAAAAAAAAAAAAAAAAAAAAAAAAAAAAAAAAAA

AAAAAAAAAAAAAAAAAAAAAAAAAAAA

The underlined portion indicates 5' UTR or 3' UTR.

[Construction of IVT (In Vitro Translation) Template DNA]

IVT template DNA was produced by mixing a 5' UTR fragment, an ORF region fragment of a marker gene, and a 3' UTR fragment, and then linking them by PCR (fusion PCR). These fragments were produced by PCR amplification, or were purchased as oligo DNAs and were then used. Hereafter, details of methods of producing four IVT template DNAs, namely, EGFP mRNA, mCherry mRNA, 1xT302b-EGFP and EGFP-4xT302b, are described.

The following PCR amplification was carried out on EGFP and mCherry gene ORF regions. Using pCTp-EGFP (Saito H, et al., Nat. Commun. 2: 160 2011) as a template, PCR amplification was carried out with TAPEGFP_IVTfwd (KEC-67) (SEQ ID NO: 5) and TAP_IVTrev (KEC-23) (SEQ ID NO: 6) to produce an EGFP_ORF fragment. Likewise, using pCR2.1-mCherry (Tanaka A, et al., PLoS One. 2013 Apr. 23; 8(4): e61540.) as a template, PCR amplification was carried out with mCherry_IVTfwd (KEC-888) (SEQ ID NO: 7) and mCherry_IVTrev (KEC-889) (SEQ ID NO: 8) to produce a mCherry_ORF fragment.

Moreover, the following PCR amplification was carried out on a 5' UTR fragment and a 3' UTR fragment that did not contain a target sequence. Using IVT 5primeUTR (KEC-62) (SEQ ID NO: 9) as a template, PCR amplification was carried out using TAP_T7_1G (KEC-876) (SEQ ID NO: 10) and Rev5UTR (KEC-1) (SEQ ID NO: 11) as primers, to produce a 5' UTR fragment. Using IVT 3primeUTR (KEC-63) (SEQ ID NO: 12) as a template, PCR amplification was carried out using Fwd3UTR (KEC-4) (SEQ ID NO: 13) and Rev3UTR2T20 (KEC-65) (SEQ ID NO: 14) as primers, to produce a 3' UTR fragment.

The IVT template DNAs of EGFP mRNA and mCherry mRNA were produced by mixing the aforementioned 5' UTR fragment, 3' UTR fragment, and EGFP_ORF fragment or mCherry_ORF fragment, and then performing fusion PCR using TAP_T7_1G and 3UTR120A (KEC-308) (SEQ ID NO: 15) as primers.

The IVT template DNA of 1xT302b-EGFP was produced by mixing 5UTR-T302b-3p (KTC-004) (SEQ ID NO: 16), the EGFP_ORF fragment, and the 3' UTR fragment, and then performing fusion PCR using GCT7CMV_del4 (KEC-97) (SEQ ID NO: 17) and 3UTR120A as primers.

The IVT template DNA of EGFP-4xT302b was produced by performing fusion PCR on the 5' UTR fragment, the EGFP_ORF fragment, and 3UTRtemp_4xT302b-3p (KTC-001) oligo DNA (SEQ ID NO: 18), using TAP_T7_1G and 3UTR120A as primers.

Production of oligo DNAs, such as the aforementioned primers and templates, was consigned to other parties, as appropriate, and the thus-produced oligo DNAs were then used. The sequences thereof are shown in Table 1.

The IVT template DNAs obtained by PCR amplification as described above were purified using MinElute PCR purification kit (QIAGEN) in accordance with the manufacturer's instructions.

TABLE 1

| Name | sequence (5' to 3') | SEQ ID NO: |
|---|---|---|
| TAPEGFP_IVTfwd (KEC-67) | CACCGGTCGCCACCTGGGATCCGTGAGCAAGGGC | 5 |
| TAP_IVTrev (KEC-23) | GCCCCGCAGAAGGTCTAGACTATCACTCGAGATG CATATGAGATC | 6 |
| mCherry_IVTfwd (KEC-888) | CACCGGTCGCCACCATGGTGAGCAAGGGCGAGGA GGAT | 7 |
| mCherry_IVTrev (KEC-889) | GCCCCGCAGAAGGTCTAGATTTACTTGTACAGCT CGTCCATG | 8 |
| IVT 5primeUTR (KEC-62) | CAGTGAATTGTAATACGACTCACTATAGGGCGAA TTAAGAGAGAAAGAAGAGTAAGAAGAAATATAAG ACACCGGTCGCCACCATG | 9 |
| TAP_T7_1G (KEC-876) | CAGTGAATTGTAATACGACTCACTATAG | 10 |
| Rev5UTR (KEC-1) | CATGGTGGCGACCGGTGTCTTATATTTCTTCTTA CTC | 11 |
| IVT 3primeUTR (KEC-63) | TCTAGACCTTCTGCGGGCTTGCCTTCTGGCCAT GCCCTTCTTCTCTCCCTTGCACCTGTACCTCTTG GTCTTTGAATAAAGCCTGAGTAGG | 12 |
| Fwd3UTR (KEC-4) | TCTAGACCTTCTGCGGGC | 13 |
| Rev3UTR2T20 (KEC-65) | TTTTTTTTTTTTTTTTTTTTCCTACTCAGGCTTT ATTCAAAGACCAAG | 14 |
| 3UTR120A (KEC-308) | TTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTTCCTACTCAGGCTTTATTCA | 15 |
| 5UTR-T302b-3p (KTC-004) | CTCACTATAGGTCAGATCCGCTAGGATCCTACTA AAACATGGAAGCACTTACACCGGTCGCCACCATG | 16 |
| GCT7CMV_del4 (KEC-97) | GCTAATACGACTCACTATAGGTCAGATCCGCTAG GATC | 17 |
| 3UTRtemp_4xT302b-3p (KTC-001) | TCTAGACCTTCTGCGGGCCTACTAAAACATGGAA GCACTTACTACTAAAACATGGAAGCACTTACTAC TAAAACATGGAAGCACTTACTACTAAAACATGGA AGCACTTATGAATAAAGCCTGAGTAGGAAAAAAA AAAAAAAAAA | 18 |

[IVT Synthesis of mRNA]

mRNA was synthesized by IVT, using protocols prepared by modifying the method described in Warren L., et al., Cell Stem Cell, 7(5): 618-30, 2010. Specifically, mRNA was prepared from the aforementioned IVT template, using MegaScript T7 kit (Ambion). At this time, pseudo uridine-5'-triphosphate and 5-methylcytidine-5'-triphosphate (Tri-Link Bio Technologies) were used, instead of using uridine triphosphate and cytidine triphosphate. Before the reaction, guanosine-5'-triphosphate was 5 times diluted with Anti Reverse Cap Analog (New England Biolabs), and was then used. The reaction mixture was incubated at 37° C. for 4 hours. Thereafter, TURBO DNase (Ambion) was added to the resultant, and the obtained mixture was further incubated at 37° C. for 30 minutes. The obtained mRNA was purified using FavorPrep Blood/Cultured Cells total RNA extraction column (Favorgen Biotech), and the resultant was then incubated at 37° C. for 30 minutes, using Antarctic Phosphatase (New England Biolabs). Thereafter, the reaction mixture was further purified using RNeasy MiniElute Cleanup Kit (QIAGEN).

[Expansive Culture of Human iPS Cells]

Human iPS cells (201B7, 409B2 and 427F1) were received from Dr. Shinya YAMANAKA, Kyoto University. The human iPS cells were cultured on MMC-treated SNL feeder cells in Primate ES cell medium (Reprocell) containing 5 ng/ml bFGF (Reprocell) and 0.5% penicillin-streptomycin (Invitrogen). When colonies of the iPS cells were increased to a certain extent, they were subjected to subculture. In the subculture, the culture solution was removed, the cells were then washed with D-PBS (Nacalai tesq), and thereafter, CTK (Collagenase type 2 (Invitrogen), 2.5% trypsin-EDTA (Nacalai tesq), and KSR (Invitrogen)) was added to the resulting cells. The mixture was washed with D-PBS twice, and the feeder cells were then removed. A culture solution was added to a culture dish from which the feeder cells had been removed, and the iPS cells were harvested using a cell scraper. Thereafter, the colonies of the iPS cells were dissociated by pipetting. The dissociated iPS cell colonies were subcultured in a novel culture dish at a ratio of 1:3. For feeder-free culture, a Matrigel (BD) coated plate or dish was used, and mTeSR1 (Stem cell technologies) was used as a medium. The culture method was applied in accordance with the manufacturer's instructions.

[Transfection with miR-302b-Responsive Reporter mRNA]

Human iPS cells were seeded on a Matrigel (BD)-coated 24-well plate. On the following day, 200 ng of EGFP mRNA or each miR-302h-responsive reporter mRNA was introduced into the iPS cells, using 1-µL StemFect (Stemgent), in accordance with the manufacturer's instructions. After completion of the introduction, in order to examine the effects of the miRNA, the cells were cultured in the presence of a 2 pmol, 0.5 pmol, or 0 pmol mirVana miRNA inhibitor (Applied Biosciences).

[Detection of Human iPS Cells Using miR-302b-Responsive Reporter mRNA]

EGFP mRNA and each miR-302b-responsive reporter mRNA were transfected into human iPS cells, and the mixture was then cultured in the presence of a mirVana miRNA inhibitor. Thereafter, the reaction mixture was analyzed by flow cytometry. The fluorescence level of EGFP was changed in both 1xT302b-EGFP and EGFP4xT302b, depending on the concentration of the mirVana miRNA inhibitor (FIG. 1). That is to say, these results suggest that the translation level of EGFP in 1xT302b-EGFP and EGFP-4xT302b is decreased by the activity of miR302b that is highly expressed in human iPS cells having pluripotency. Accordingly, the results demonstrated the possibility that cells having lost their pluripotency after induction of the differentiation, which are included in a cell population, can be specifically recognized by using miR-302b-responsive reporter mRNA.

Figure 2:
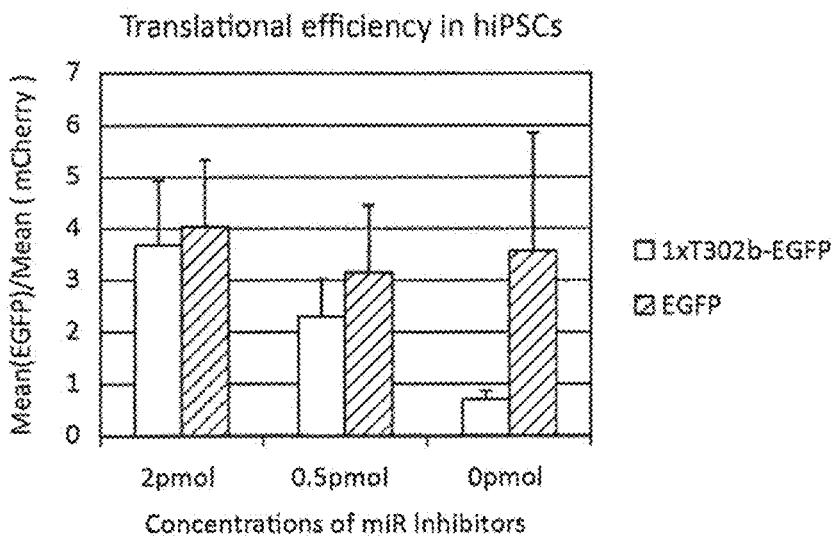
FIG. 2 shows the results obtained by measuring the fluorescence intensity of EGFP to the fluorescence intensity of mCherry in iPS cells, into which mCherry and EGFP, or mCherry and 1xT302b-EGFP have been co-introduced, and which have been then cultured in a medium, to which a mirVana miRNA inhibitor had been added in different concentrations. In the figure, the error bar indicates an average±standard deviation (n=3).

[Translation Efficiency of miR-302b-Responsive Reporter mRNA]

mCherry mRNA and EGFP or 1xT302b-EGFP were co-introduced into human iPS cells (201B7), and they were then cultured in the presence of a mirVana miRNA inhibitor. Thereafter, the fluorescence intensity of each of EGFP and mCherry was measured by flow cytometry, and the ratio of the fluorescence intensity of EGFP to the fluorescence intensity of mCherry was then calculated. As a result, it was confirmed that when the activity of miRNA was suppressed by the mirVana miRNA inhibitor, the fluorescence intensity of EGFP that is corrected by the fluorescence intensity of mCherry in EGFP, and the fluorescence intensity of EGFP in 1xT302b-EGFP were at the same levels as each other, but that when the activity of miRNA was not suppressed, the fluorescence intensity of EGFP in 1xT302b-EGFP was significantly decreased (FIG. 2). From these results, it was confirmed that the fluorescence intensity of EGFP is decreased in iPS cells, not because of poor introduction efficiency of 1xT302b-EGFP, but because of the activity of miRNA. The same results as those described above were obtained even using other iPS cell lines (409B2 and 427F1).

Example 2

[Sorting of Differentiation-Induced Cells]

Figure 3:
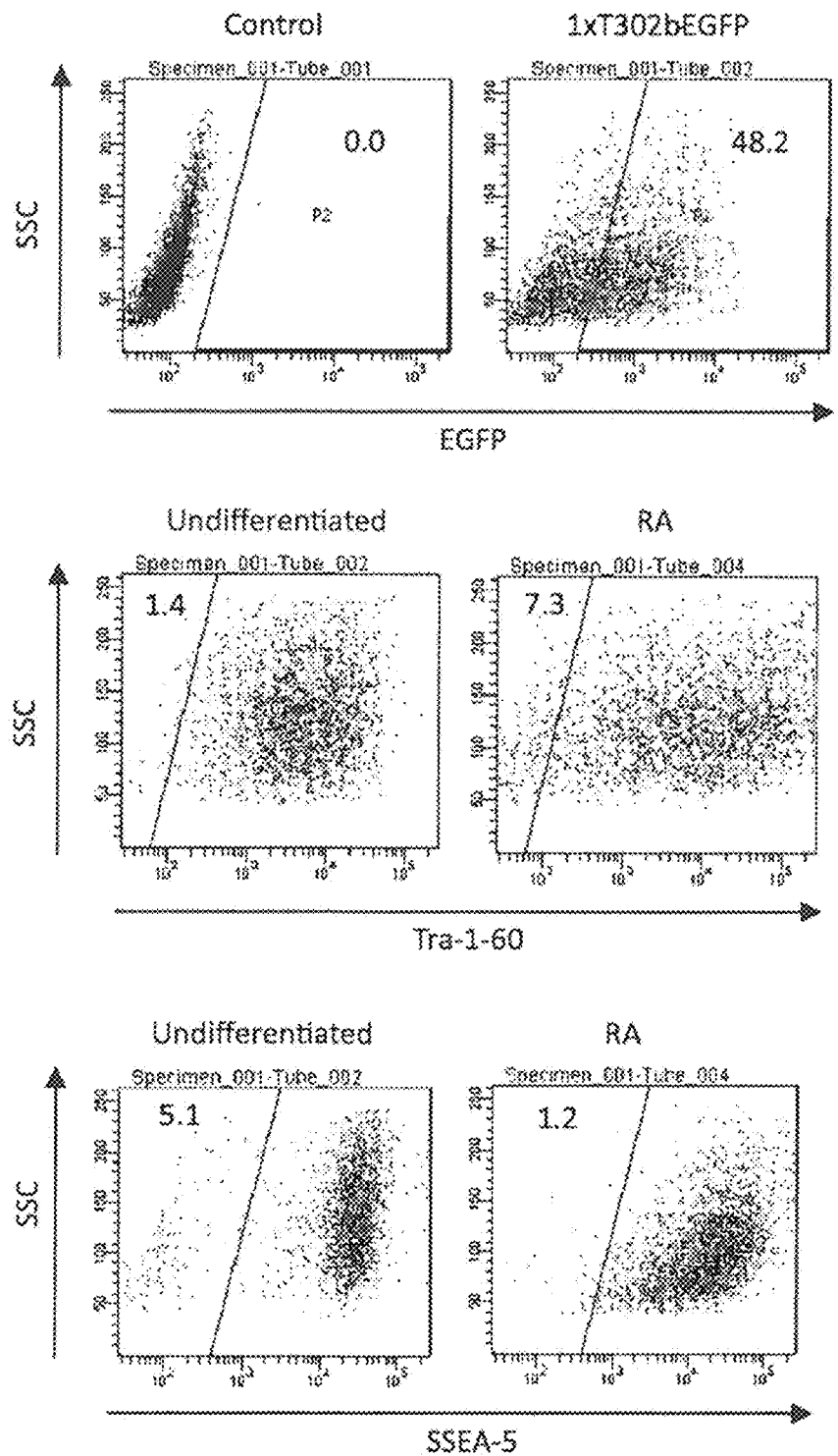
FIG. 3 shows the results obtained by measuring by flow cytometry the fluorescence intensity of EGFP in iPS cells, which have been cultured in a retinoic acid medium, and into which 1xT302b-EGFP has not been introduced or has been introduced (upper view), the results obtained by measuring by flow cytometry the expression level of Tra-1-60 in iPS cells, or in iPS cells cultured in a retinoic acid medium (central view), and the results obtained by measuring by flow cytometry the expression level of SSEA5 in iPS cells, or in iPS cells cultured in a retinoic acid medium (lower view). The number shown in the figure indicates the content rate to the entire cells in the described fraction.
Figure 4:
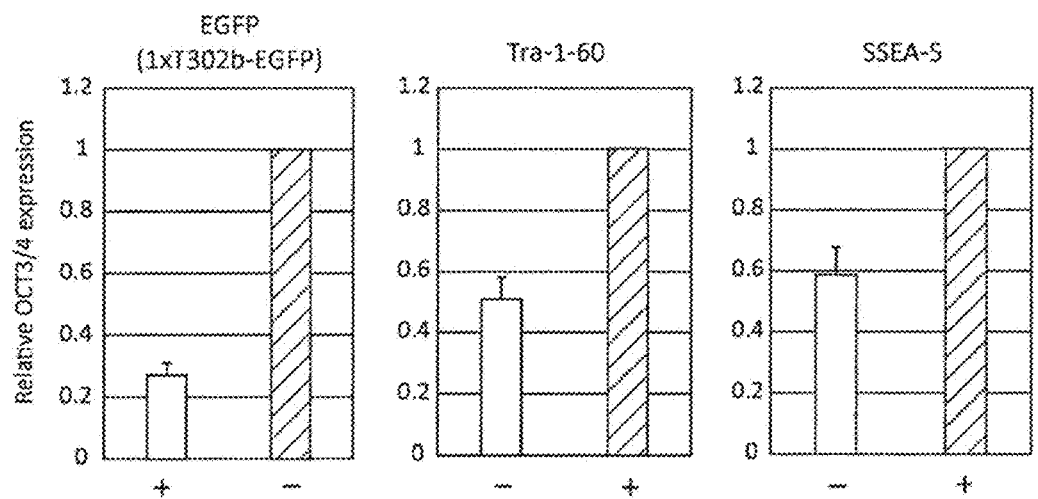
FIG. 4 shows the expression level of OCT3/4 in EGFP-positive cells (+) or EGFP-negative cells (−) in iPS cells, which have been cultured in a retinoic acid medium and into which 1xT302b-EGFP has been then introduced (left view), the expression level of OCT3/4 in Tra1-60-negative cells (−) or Tra-1-60-positive cells (+) in iPS cells, which have been cultured in a retinoic acid medium (central view), and the expression level of OCT3/4 in SSEA5-negative cells (−) or SSEA5-positive cells (+) in iPS cells, which have been cultured in a retinoic acid medium (right view).

Human iPS cells were seeded on a Matrigel (BD)-coated 10 cm dish, and were then cultured in a retinoic acid medium (DMEM-F12 (Invitrogen) containing 0.5 uM retinoic acid (Sigma), 10% FBS (GIBCO), 0.5% Penicillin-streptomycin (Invitrogen), % Glutamax (Invitrogen), and 1% NEAA (Invitrogen)) for 3 days (Tang C, et al., Nature Biotechnology, 29(9): 829-34, 2011). After completion of the culture, the cells were separated from the culture dish, and were then seeded again on a Matrigel-coated 10 cm dish containing mTeSR1 medium (Stem cell technologies) or the same medium as described above. On the following day, 1xT302b-EGFP was transfected into the cells. The transfection was carried out using 24 µl of stemfect (Stemgent) in accordance with the manufacturer's instructions. Twenty-four hours after the transfection, the resulting cells were separated from the culture dish, and the fluorescence intensity of EGFP was then analyzed by flow cytometry. At this time, RA-treated cells or RA-not-treated cells were also measured using an anti-Tra-1-60 antibody (Alexa647, BD) or an anti-SSEA5 antibody (8e11, GeneTex), and individual surface markers were also analyzed. As a result, some RA-treated cells were negative to Tra-1-60. The same results as those described above were obtained also regarding SSEA5 (FIG. 3). On the other hand, among the cells, which had been treated with RA and into which 1xT302b-EGFP had been introduced, some EGFP-positive cells were confirmed. Furthermore, the expression level of OCT3/4, in each of EGFP-positive or negative, Tra-1-60-positive or -negative, and SSEA5-positive or -negative cells, was measured by quantitative PCR. As a result, it was confirmed that the expression level of OCT3/4 was decreased in EGFP-positive cells, when compared with in EGFP-negative cells (FIG. 4). Thus, It was suggested that the cells, into which 1xT302b-EGFP had been introduced and were positive to EGFP, are differentiated cells. Further, the ratio of the expression of EGFP-positive cells to EGFP-negative cells was lower than the ratio of the expression of Tra-1-60-negative cells to Tra-1-60-positive cells, or the ratio of the expression of SSEA5-negative cells to SSEA5-positive cells. These results demonstrated the possibility that differentiated cells can be extracted with EGFP involving the use of 1xT302b-EGFP, with higher sensitivity than in the case of using an anti-Tra-1-60 antibody or an anti-SSEA5 antibody.

Figure 5:
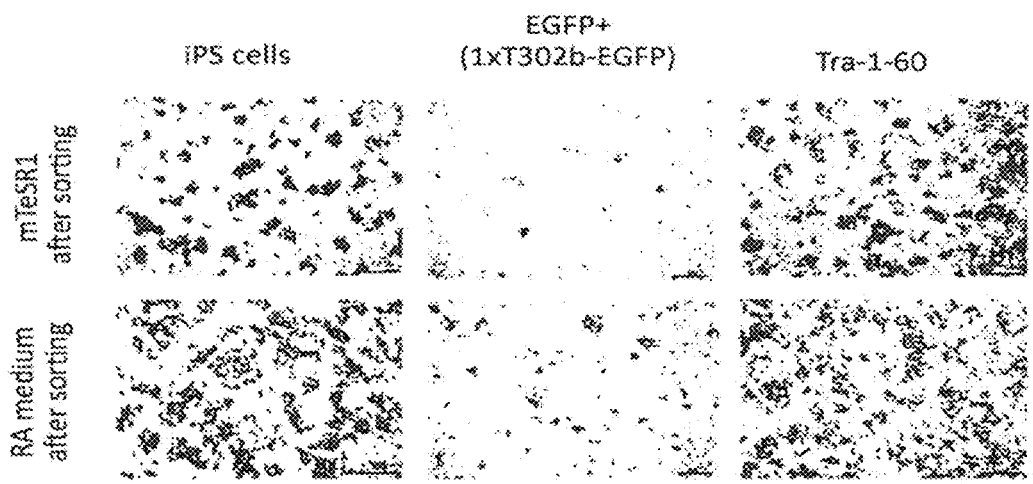
FIG. 5 shows alkaline phosphatase-stained images of cells obtained by culturing iPS cells in a retinoic acid medium, then introducing 1xT302b-EGFP into the cultured cells, and then culturing EGFP-positive cells or Tra-1-60-negative cells in the resulting cells in mTeSR1 (upper view) or in a retinoic acid medium (lower view) for 5 days.

Subsequently, according to flow cytometry, the separated EGFP-positive cells or Tra-1-60-negative cells were seeded on a Matrigel-coated 6-well-plate, and were then cultured in an mTeSR1 medium or in a retinoic acid medium for 5 days. At this time, the medium was replaced with fresh medium every other day. The obtained cells were stained using an alkaline phosphatase staining kit (Sigma). In the case of EGFP-positive cells into which 1xT302b-EGFP had been transfected, the remaining amount of alkaline phosphatase-stained positive cells (undifferentiated cells) was significantly decreased (FIG. 5). Thus, it was demonstrated that, by using 1xT302b-EGFP, differentiated cells can be selectively sorted out from a cell population comprising both undifferentiated cells and differentiated cells, without the mixing of the undifferentiated cells. On the other hand, it was confirmed that the sorted Tra-1-60-negative cells are likely to include undifferentiated cells.

Figure 6:
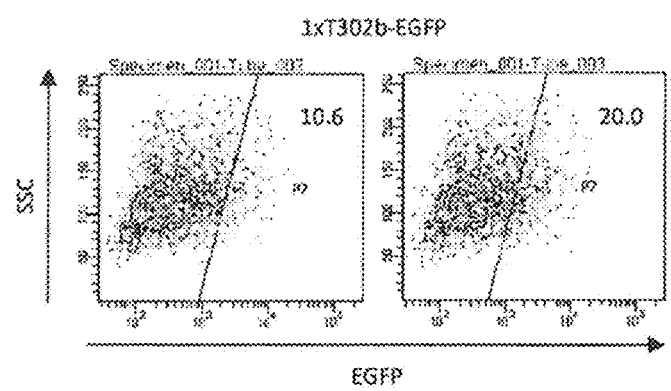
FIG. 6A shows the results obtained by measuring by flow cytometry the expression level of EGFP in iPS cells, which have been cultured in a retinoic acid medium and into which 1xT302b-EGFP has been introduced.
FIG. 6B shows alkaline phosphatase-stained images of cells obtained by culturing iPS cells in a retinoic acid medium, then introducing 1xT302b-EGFP into the cultured cells, and then culturing the top 10% EGFP-positive cells or the top 20% EGFP-positive cells, among the resulting cells, in mTeSR1 (upper view) or in a retinoic acid medium (lower view) for 5 days.
Figure 6:
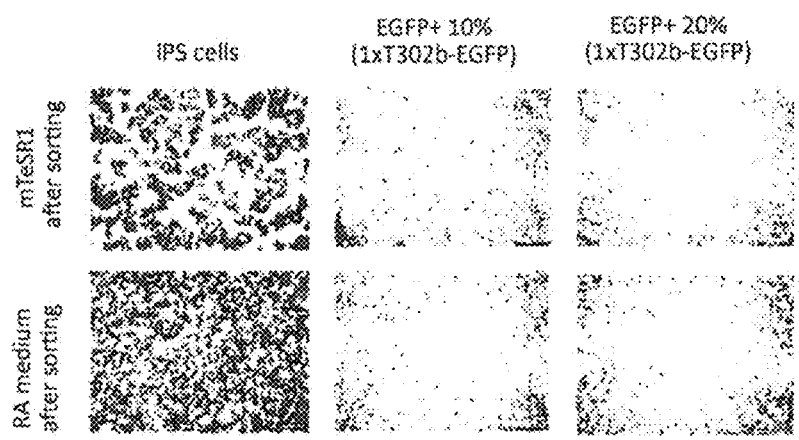

Subsequently, in order to realize complete removal of undifferentiated cells, the top 10% EGFP-positive cells, and the top 20% EGFP-positive cells were sorted by flow cytometry (FIG. 6A). Sort samples were cultured for 5 days by the aforementioned method, and were then stained with alkaline phosphatase. As a result, completely no undifferentiated cells stained with alkaline phosphatase were found in both the top 10% EGFP-positive cells and the top 20% EGFP cells (FIG. 6B). Accordingly, it was demonstrated that undifferentiated cells are not included even in the top 20% EGFP-positive cells.

Example 3

[Designing of 302a-5p- and -367-3p-Responsive Reporter mRNAs]

hmAG1-mRNA (SEQ ID NO: 19), which encodes the fluorescence reporter gene hmAG1 and includes the five prime end untranslated region (5' UTR) and the three prime end untranslated region (3' UTR) of α globin, was modified, and miR-302a-5p-responsive reporter mRNA (SEQ ID NO: 20) comprising one copy of the target sequence of miR-302a-5p in the 5' UTR and miR-367-3p-responsive reporter mRNA (SEQ ID NO: 21) comprising one copy of the target sequence of miR367-3p in the 5' UTR were each designed. Moreover, in order to normalize transfection, tagBFP mRNA (SEQ ID NO: 22) comprising the 5' UTR and 3' UTR of α globin, which was to be used as a control, was also designed. Furthermore, as a drug resistance gene, Puromycin R-mRNA (SEQ ID NO: 23) comprising a puromycin resistance gene was modified, and 302a-5p-responsive Puromycin R-mRNA (SEQ ID NO: 24) comprising one copy of the target sequence of miR-302a-5p in the 5' UTR was designed. These gene sequences of mRNAs are shown below.

Gene sequence of hmAG1-mRNA
(SEQ ID NO: 19)
<u>GGGCGAATTAAGAGAGAAAAGAAGAGTAAGAAGAAATATAAGACACCGGT</u>

<u>CGCCACC</u>atgGTGAGCGTGATCAAGCCCGAGATGAAGATCAAGCTGTGCA

TGAGGGGCACCGTGAACGGCCACAACTTCGTGATCGAGGGCGAGGGCAAG

GGCAACCCCTACGAGGGCACCCAGATCCTGGACCTGAACGTGACCGAGGG

CGCCCCCCTGCCCTTCGCCTACGACATCCTGACCACCGTGTTCCAGTACG

GCAACAGGGCCTTCACCAAGTACCCCGCCGACATCCAGGACTACTTAAGC

AGACCTTCCCCGAGGGCTACCACTGGGAGAGGAGCATGACCTACGAGGAC

CAGGGCATCTGCACCGCCACCAGCAACATCAGCATGAGGGGCGACTGCTT

CTTCTACGACATCAGGTTCGACGGCACCAACTTCCCCCCCAACGGCCCCG

TGATGCAGAAGAAGACCCTGAAGTGGGAGCCCAGCACCGAGAAGATGTAC

GTGGAGGACGGCGTGCTGAAGGGCGACGTGAACATGAGGCTGCTGCTGGA

GGGCGGCGGCCACTACAGGTGCGACTTCAAGACCACCTACAAGGCCAAGA

AGGAGGTGAGGCTGCCCGACGCCCACAAGATCGACCACAGGATCGAGATC

CTGAAGCACGACAAGGACTACAACAAGGTGAAGCTGTACGAGAACGCCGT

GGCCAGGTACTCCATGCTGCCCAGCCAOGCCAAGtga<u>ATCTAGACCTTCT</u>

<u>GCGGGGCTTGCCTTCTGGCCATGCCCTTCTTCTCTCCCTTGCACCTGTAC</u>

<u>CTCTTGGTCTTTGAATAAAGCCTGAGTAGGAAAAAAAAAAAAAAAAAAAA</u>

<u>AAAAAAAAAAAAAAAAAAAAAAAAAAAAAAAAAAAAAAAAAAAAAAAAA</u>

<u>AAAAAAAAAAAAAAAAAAAAAAAAAAAAAAAAAAAAAAAAAAAAA</u>

The initiation codon and the termination codon are indicated with lowercase letters. The underlined portion indicates 5' UTR or 3' UTR.

Gene sequence of 302a-5p-responsive hmAG1-mRNA
(SEQ ID NO: 20)
<u>GGTTCCGCGATCGCGGATCCagcaagtacatccacgtttaagtAGATCCA</u>

<u>CCGGTCGCCACC</u>atgGTGAGCGTGATCAAGCCCGAGATGAAGATCAAGCT

GTGCATGAGGGGCACCGTGAACGGCCACAACTTCGTGATCGAGGGCGAGG

GCAAGGGCAACCCCTACGAGGGCACCCAGATCCTGGACCTGAACGTGACC

GAGGGCGCCCCCCTGCCCTTCGCCTACGACATCCTGACCACCGTGTTCCA

GTACGGCAACAGGGCCTTCACCAAGTACCCCGCCGACATCCAGGACTACT

TCAAGCAGACCTTCCCCGAGGGCTACCACTGGGAGAGGAGCATGACCTAC

GAGGACCAGGGCATCTGCACCGCCACCAGCAACATCAGCATGAGGGGCGA

CTGCTTCTTCTACGACATCAGGTTCGACGGCACCAACTTCCCCCCCAACG

GCCCCGTGATGCAGAAGAAGACCCTGAAGTGGGAGCCCAGCACCGAGAAG

ATGTACGTGGAGGACGGCGTGCTGAAGGGCGACGTGAACATGAGGCTGCT

GCTGGAGGGCGGCGGCCACTACAGGTGCGACTTCAAGACCACCTACAAGG

CCAAGAAGGAGGTGAGGCTGCCCGACGCCCACAAGATCGACCACAGGATC

GAGATCCTGAAGCACGACAAGGACTACAACAAGGTGAAGCTGTACGAGAA

CGCCGTGGCCAGGTACTCCATGCTGCCCAGCCAGGCCAAGtga<u>ATCTAGA</u>

<u>CCTTCTGCGGGGCTTGCCTTCTGGCCATGCCCTTCTTCTCTCCCTTGCAC</u>

<u>CTGTACCTCTTGGTCTTTGAATAAAGCCTGAGTAGGAAAAAAAAAAAAAA</u>

<u>AAAAAAAAAAAAAAAAAAAAAAAAAAAAAAAAAAAAAAAAAAAAAAAAA</u>

<u>AAAAAAAAAAAAAAAAAAAAAAAAAAAAAAAAAAAAAAAAAAAAAAAAA</u>

<u>AAAAAA</u>

The initiation codon and the termination codon are indicated with small letters, and the miRNA target sequence is indicated with lowercase letters. The underlined portion indicates 5' UTR or 3' UTR.

Gene sequence of 367-3p-responsive hmAG1-mRNA
(SEQ ID NO: 21)
<u>GGTTCCGCGATCGCGGATCCtcaccattgctaaagtacaattAGATCACA</u>

<u>CCGGTCGCCACC</u>atgGTGAGCGTGATCAAGCCCGAGATGAAGATCAAGCT

GTGCATGAGGGGCACCGTGAACGGCCACAACTTCGTGATCGAGGGCGAGG

GCAAGGGCAACCCCTACGAGGGCACCCAGATCCTGGACCTGAACGTGACC

GAGGGCGCCCCCCTGCCCTTCGCCTACGACATCCTGACCACCGTGTTCCA

GTACGGCAACAGGGCCTTCACCAAGTACCCCGCCGACATCCAGGACTACT

TCAAGCAGACCTTCCCCGAGGGCTACCACTGGGAGAGGAGCATGACCTAC

GAGGACCAGGGCATCTGCACCGCCACCAGCAACATCAGCATGAGGGGCGA

CTGCTTCTTCTACGACATCAGGTTCGACGGCACCAACTTCCCCCCCAACG

GCCCCGTGATGCAGAAGAAGACCCTGAAGTGGGAGCCCAGCACCGAGAAG

ATGTACGTGGAGGACGGCGTGCTGAAGGGCGACGTGAACATGAGGCTGCT

GCTGGAGGGCGGCGGCCACTACAGGTGCGACTTCAAGACCACCTACAAGG

CCAAGAAGGAGGTGAGGCTGCCCGACGCCCACAAGATCGACCACAGGATC

GAGATCCTGAAGCACGACAAGGACTACAACAAGGTGAAGCTGTACGAGAA

CGCCGTGGCCAGGTACTCCATGCTGCCCAGCCAGGCCAAGtga<u>ATCTAGA</u>

<u>CCTTCTGCGCGGCTTGCCTTCTGGCCATGCCCTTCTTCTCTCCCTTGCAC</u>

<u>CTGTACCTCTTGGTCTTTGAATAAAGCCTGAGTAGGAAAAAAAAAAAAAA</u>

<u>AAAAAAAAAAAAAAAAAAAAAAAAAAAAAAAAAAAAAAAAAAAAAAAAA</u>

<u>AAAAAAAAAAAAAAAAAAAAAAAAAAAAAAAAAAAAAAAAAAAAAAAAA</u>

<u>AAAAAA</u>

The initiation codon and the termination codon are indicated with lowercase letters, and the miRNA target sequence is indicated with lowercase letters. The underlined portion indicates 5' UTR or 3' UTR.

Gene sequence of tagBFP-mRNA
(SEQ ID NO: 22)
GGGCGAATTAAGAGAGAAAAGAAGAGTAAGAAGAAATATAAGACACCGGT CGCCACCatgGGATCCAGCGAGCTGATTAAGGAGAACATGCACATGAAGC

TGTACATGGAGGGCACCGTGGACAACCATCACTTCAAGTGCACATCCGAG

GGCGAAGGCAAGCCCTACGAGGGCACCCAGACCATGAGAATCAAGGTGGT

CGAGGGCGGCCCTCTCCCCTTCGCCTTCGACATCCTGGCTACTAGCTTCC

TCTACGGCAGCAAGACCTTCATCAACCACACCCAGGGCATCCCCGACTTC

TTTCAAGCAGTCCTTCCCTGAGGGCTTCACATGGGAGAGAGTCACCACAT

ACGAAGACGGGGGCGTGCTGACCGCTACCCAGGACACCAGCCTCCAGGAC

GGCTGCCTCATCTACAACGTCAAGATCAGAGGGGTGAACTTCACATCCAA

CGGCCCTGTGATGCAGAAGAAAACACTCGGCTGGGAGGCCTTCACCGAGA

CGCTGTACCCCGCTGACGGCGGCCTGGAAGGCAGAAACGACATGGCCCTG

AAGCTCGTGGGCGGGAGCCATCTGATCGCAAACATCAAGACCACATATAG

ATCCAAGAAACCCGCTAAGAACCTCAAGATGCCTGGCGTCTACTATGTGG

ACTACAGACTGGAAAGAATCAAGGAGGCCAACAACGAGACCTACGTCAG

CAGCACGAGGTGGCAGTGGCCAGATACTGCGACCTCCCTAGCAAACTGGG

GCACAGATCTCATATGCATCTCGAGtgaTCTAGACCTTCTGCGGGGCTTG

CCTTCTGGCCATGCCCTTTCTTCTCTCCCTTGCACCTGTACCTCTTGGTC

TTTGAATAAAGCCTGAGTAGGAAAAAAAAAAAAAAAAAAAAAAAAAAAAA

AAAAAAAAAAAAAAAAAAAAAAAAAAAAAAAAAAAAAAAAAAAAAAAAA

AAAAAAAAAAAAAAAAAAAAAAAAAAAAAAAAAAAAAAAAAA

The initiation codon and the termination codon are indicated with lowercase letters, and the underlined portion indicates 5' UTR or 3' UTR.

Gene sequence of Puromycin R-mRNA
(SEQ ID NO: 23)
GGGCGAATTAAGAGAGAAAAGAAGAGTAAGAAGAAATATAAGACACCGG TCGCCACCatgACCGAGTACAAGCCCACGGTGCGCCTCGCCACCCGCGA

CGACGTCCCCAGGGCCGTACGCACCCTCGCCGCCGCGTTCGCCGACTAC

CCCGCCACGCGCCACACCGTCGATCCGGACCGCCACATCGAGCGGGTCA

CCGAGCTGCAAGAACTCTTCCTCACGCGCGTCGGGCTCGACATCGGCAA

GGTGTGGGTCGCGGACGACGGCGCCGCGGTGGCGGTCTGGACCACGCCG

GAGAGCGTCGAAGCGGGGGCGGTGTTCGCCGAGATCGGCCCGCGCATGG

CCGAGTTGAGCGGTTCCCGGCTGGCCGCGCAGCAACAGATGGAAGGCCT

CCTGGCGCCGCACCGGCCCAAGGAGCCGCGTGGTTCCTGGCCACCGTC

GGCGTCTCGCCCGACCACCAGGGCAAGGGTCTGGGCAGCGCCGTCGTGC

TCCCCGGAGTGGAGGCGGCCGAGCGCGCCGGGGTGCCCGCCTTCCTGGA

GACCTCCGCGCCCCGCAACCTCCCCTTCTACGAGCGGCTCGGCTTCACC

GTCACCGCCGACGTCGAGGTGCCCGAAGGACCGCGCACCTGGTGCATGA

CCCGCAAGCCCGGTGCCtgaTCTAGACCTTCTGCGGGGCTTGCCTTCTG

GCCATGCCCTTCTTCTCTCCCTTGCACCTGTACCTCTTGGTCTTTGAAT

AAAGCCTGAGTAGGAAAAAAAAAAAAAAAAAAAAAAAAAAAAAAAAAAA

AAAAAAAAAAAAAAAAAAAAAAAAAAAAAAAAAAAAAAAAAAAAAAAAA

AAAAAAAAAAAAAAAAAAAAAAAAAAAAAAAAAAAAAAAA

The initiation codon and the termination codon are indicated with lowercase letters. The underlined portion indicates 5' UTR or 3' UTR.

Gene sequence of 302a-5p-responsive Puromycin R-mRNA
(SEQ ID NO: 24)
GGTTCCGCGATCGCGGATCCagcaagtacatccacctttaagtAGATCCA CCGGTCGCCACCatgACCGAGTACAAGCCCACGGTGCGCCTCGCCACCCG

CGACGACGTCCCCAGGGCCGTACGCACCCTCGCCGCCGCGTTCGCCGACT

ACCCCGCCACGCGCCACACCGTCGATCCGGACCGCCACATCGAGCGGGTC

ACCGAGCTGCAAGAACTCTTCCTCACGCGCGTCGGGCTCGACATCGGCAA

GGTGTGGGTCGCGGACGACGGCGCCGCGGTGGCGGTCTGGACCACGCCGG

AGAGCGTCGAAGCGGGGGCGGTGTTCGCCGAGATCGGCCCGCGCATGGCC

GAGTTGAGCGGTTCCCGGCTGGCCGCGCAGCAACAGATGGAAGGCCTCCT

GGCGCCGCACCGGCCCAAGGAGCCGCGTGGTTCCTGGCCACCGTCCGCG

TCTCGCCCGACCACCAGGGCAAGGGTCTGGGCAGCGCCGTCGTGCTCCCC

GGAGTGGAGGCGGCCGAGCGCGCCGGGGTGCCCGCCTTCCTGGAGACCTC

CGCGCCCCGCAACCTCCCCTTCTACGAGCGGCTCGGCTTCACCGTCACCG

CCGACGTCGAGGTGCCCGAAGGACCGCGCACCTGGTGCATGACCCGCAAG

CCCGGTGCCtgaTCTAGACCTTCTGCGGGGCTTGCCTTCTGGCCATGCCC

TTCTTCTCTCCCTTGCACCTGTACCTCTTGGTCTTTGAATAAAGCCTGAG

TAGGAAAAAAAAAAAAAAAAAAAAAAAAAAAAAAAAAAAAAAAAAAAAAA

AAAAAAAAAAAAAAAAAAAAAAAAAAAAAAAAAAAAAAAAAAAAAAAAAA

AAAAAAAAAAAAAAAAAAAAAA

The initiation codon and the termination codon are indicated with lowercase letters, and the miRNA target sequence is indicated with lowercase letters. The underlined portion indicates 5' UTR or 3' UTR.

[Production of Templates and In Vitro Transcription (IVT)]

IVT template DNAs were produced by mixing a 5' UTR fragment, an ORF region, fragment of a marker gene, and a 3' UTR fragment, and then linking them by PCR (fusion PCR) in the same manner as that of Example 1. These fragments were produced by PCR amplification. Hereafter, details of methods of producing six IVT template DNAs, namely, hmAG1, 302a-5p-responsive hmAG1, 367-3p-responsive hmAG1, tagBFP, Puromycin R, and 302a-5p-responsive Puromycin R, are described.

The following PCR amplification was carried out on the ORF regions of hmAG1, tagBFP and Puromycin R genes. Using Plasmid template: S/G2/M Green (Amalgam MBL) as a template, PCR amplification was carried out with hmAG1_IVTfwd (KEC-330) (SEQ ID NO: 25) and hmAG1_IVTrev (KEC-331) (SEQ ID NO: 26) to produce an hmAG1_ORF fragment. Likewise, using Plasmid template: pTAP_tagBFP (Miki et al., Cell Stem Cell, volume 16, Issue 6, 4 Jun. 2015, pages 699-711) as a template, PCR amplification was carried out with tagBFP_fwd (KED-90) (SEQ ID NO: 33) and TAP_IVTrev (KEC-23) to produce a tag- BFP_ORF fragment. Likewise, using Plasmid template: pPyCAG-Nanog-IP (plasmid 13838, Addgene) as a template, PCR amplification was carried out with ORF_PuroR_fwd (STC-035) (SEQ ID NO: 31) and ORF_PuroR_rev (STC-036) (SEQ ID NO: 32) to produce a tagBFP_ORF fragment.

Moreover, the following PCR amplification was carried out on a 5' UTR fragment and a 3' UTR fragment that did not contain a target sequence. Using IVT 5primeUTR (KEC-62) as a template, PCR amplification, was carried out using TAP_T73GC (SKC-111) (SEQ ID NO: 30) and Rev5UTR (KEC-1) (SEQ ID NO: 11) as primers, to produce a 5' UTR fragment. Using IVT 3primeUTR (KEC-63) as a template, PCR amplification was carried out using Fwd3UTR (KEC-4) and Rev3UTR2T20 (KEC-65) as primers, to produce a 3' UTR fragment.

Furthermore, the following PCR amplification was earned out on 5' UTR containing a 302a-5p target sequence, and 5' UTR containing a 367-3p target sequence. Using 5UTRtemp_T302a-5p (KEC-653) (SEQ ID NO: 27) as a template, PCR amplification was carried out using GCT7pro_5UTR2 (KEC-948) (SEQ ID NO: 29) and Rev5UTR (KEC-1) as primers, to produce a 302a-5p-5' UTR fragment. Using 5UTRtemp_T367-3p (KEC-845) (SEQ ID NO: 28) as a template, PCR amplification was carried out using GCT7pro_5UTR2 (KEC-948) and Rev5UTR (KEC-1) as primers, to produce a 367-3p-5' UTR fragment.

The IVT template DNAs of hmAG1 mRNA, tagBFP mRNA, and Puromycin R mRNA were produced by mixing the aforementioned 5' UTR fragment and 3' UTR fragment, and hmAG1_ORF fragment, tagBFP_ORF fragment or Puromycin R_ORF fragment, and then performing fusion PCR using TAP_T73GC (SKC-111) and 3UTR120A (KEC-308) as primers.

The IVT template DNAs of 302a-5p-responsive hmAG1 and 367-3p-responsive hmAG1 were produced by mixing the aforementioned 302a-5p-5' UTR fragment or 367-3p-5' UTR fragment, 3' UTR fragment, and hmAG1_ORF fragment, and then performing fusion PCR using GCT7pro_5UTR2 (KEC-948) and 3UTR120A (KEC-308) as primers. The IVT template DNA of 302a-5p-responsive Puromycin R was produced by mixing the aforementioned 302a-5p-5' UTR fragment, 3' UTR fragment, and Puromycin R_ORF fragment, and then performing fusion PCR using GCT7pro_5UTR2 (KEC-948) and 3UTR120A (KEC-308) as primers.

Production of oligo DNAs, such as the aforementioned primers and templates, was consigned to other parties, as appropriate, and the thus produced oligo DNAs were then used. The sequences thereof are shown in Table 1 and Table 2.

As described above, the IVT template DNAs obtained by PCR amplification were purified using MinElute PCR purification kit (QIAGEN) in accordance with the manufacturer's instructions. mRNA was synthesized by IVT in the same manner as that of Example 1.

TABLE 2

| hmAG1_IVTfwd (KEC-330) | CACCGGTCGCCACCATGGTGAGCGTGATCAA GCCCG 25 |
|---|---|
| hmAG1_IVT (KEC-331) | GCCCCGCAGAAGGTCTAGATTCACTTGGCCT GGCTGGGC 26 |
| 5UTRtemp_T302a-5p (KEC-653) | CGACTCACTATAGGTTCCGCGATCGCGGATC CAGCAAGTACATCCACGTTTAAGTAGATCCA CCGGTCGCCACCATG 27 |
| 5UTRtemp_T367-3p (KEC-845) | CGACTCACTATAGGTTCCGCGATCGCGGATC CTCACCATTGCTAAAGTGCAATTAGATCACA CCGGTCGCCACCATG 28 |
| GCT7pro_5UTR2 (KEC-948) | GCTAATACGACTCACTATAGGTTCCTTAATC GCGGATCC 29 |
| TAP_T73GC (SKC-111) | CAGTGAATTGTAATACGACTCACTATAGGGC 30 |
| ORF_PuroR_fwd (STC-035) | CACCGGTCGCCACCATGaccgagtacaagcc cacg 31 |
| ORF_PuroR_rev (STC-036) | GCCCCGCAGAAGGTCTAGAtcaggcaccggg cttgc 32 |
| tagBFP_fwd (KED-90) | CACCGGTCGCCACCATGGGATCCAGCGAG 33 |

[Maintenance of Feeder-Free Human iPS Cells]

Feeder-free human iPS cells (Ff-hiPSC) were maintained on iMatrix-511(E8) (Nippi, Inc.) in a StemFit (+bGF) medium in accordance with the protocols of Nakagawa et at, 2014. The human iPS cells were subcultured every eight days. Before such subculture, a 6-well plate was coated with iMatrix-511(E8) that had been diluted to a concentration of 0.5 µg/cm$^2$ with sterilized PBS, over at least 1 hour at 37° C. After completion of the coating, PBS was aspirated, and it was promptly exchanged with 1.5 ml of StemFit containing a 10 µM ROCK inhibitor (Y-26732). In order to harvest the human iPS cells, the old medium was aspirated, and the cells were then washed with 1 ml of PBS. After aspiration of PBS, 0.3 ml of a TrypSELECT solution was poured into each well, and the plate was then transferred into an incubator. One minute later, unnecessary solution was removed (move the volume over the cell), and the residue was further incubated for 3 minutes. Subsequently, the reaction mixture was removed from the incubator, the TrypSELECT solution was then aspirated, and the resultant was then washed with 1 ml of PBS. Thereafter, PBS was aspirated, and 1.5 ml of StemFit, together with a ROCK inhibitor, was added to each well. The cells were harvested using a rubber scraper, and were then pipetted using a P1000 pipette 10 times to obtain a unicellular solution. The cell density was calculated using trypan blue staining and Cell Countess (Invitrogen), and the cells were then seeded to a cell count of 1.3×10$^4$/well, so that the cells were uniformly distributed. Twenty-four hours later, the StemFit was exchanged with StemFit that did not contain a ROCK inhibitor, and thereafter, the StemFit was replaced with fresh medium every other day.

[Differentiation of Feeder-Free Human iPS Cells Into Midbrain Dopamine Neuron Cells]

Induction of the differentiation of feeder-free human iPS cells into midbrain dopamine neuron cells was carried out according to the method described in Doi, D. et al., Stem Cells 30, 935-945 (2012), A 6-well plate was coated in human iPS cells in the same manner as that described above, and 4 ml of a day 0 differentiation medium was then added to each well. Differentiation was initiated by seeding a cell solution, in which single-type-human iPS cells had been suspended in a day 0 differentiation medium containing no ROCK Inhibitors, on a 6-well place at a cell density of 5×10$^6$/well. The plate was gently stirred before it was returned into an incubator. Twenty-four hours later, the entire medium was replaced with a day 1 medium. Likewise, the medium was replaced every day. In the medium replacement from the day 0 differentiation medium to a day 2 differentiation medium, 4 ml of a medium was added to each well; in the medium replacement from a day 3 differentiation medium to a day 6 differentiation medium, 6 ml of a medium was added to each well; in the medium replacement from a day 7 differentiation medium to a day 8 differentiation medium, 8 ml of a medium was added to each well; and in the medium replacement from a day 9 differentiation medium to a day 11 differentiation medium, 10 ml of a medium was added to each well. During 11 days after completion of the culture, the cell count was increased by 2 times, and the cell density became approximately $10 \times 10^6$/well. The cells were subcultured on day 12, day 20, and day 29, and were seeded at a cell density of $5 \times 10^6$/well on a 6-well plate. After day 12, the cells were always maintained in a Neurobasal B27 medium. The medium was replaced with fresh medium every day, and 5 ml/well of a fresh medium was added every time.

[Evaluation of Differentiation Efficiency]

Regarding each subculture performed on day 12, day 20, and day 29, bulk cells were stained with a CORIN antibody (Kan Research), a floor plate marker, and a PSA-NCAM antibody, which were for use in labeling neural lineages, and the differentiation efficiency of the cells was then evaluated. At the same time, approximately $5 \times 10^5$ cells in 200 μl of a staining buffer (HBSS: Hanks' balanced salt solution/2% knockout serum, 50 μg/ml penicillin/streptomycin, 10 μM Y-26732), to which a ROCK inhibitor had been added, was subjected to a stained antigen-antibody reaction, using either a 1/200 mouse anti-human CORIN antibody (Kan Research) or a 1/100 mouse monoclonal anti-human PSA-NCAM antibody (MAB5324, Millipore). An Alexa 488-conjugated anti-mouse IgG antibody or IgM was used for secondary staining, at a ratio of 1/400 with respect to the CORIN antibody and the PSA-NCAM. The cells were stained at 4° C. for 30 minutes. The cells were stained twice in a HBSS medium. Dead cells were stained with 7-AAD for 10 minutes and were then subjected to FACS analysis.

The cells were measured by BD FACS aria-II or BD Accuri, using a FITC standard filter and a 7-AAD signal. In order to eliminate dead cells, a gate was established based on SSC-A intensity (P1), and the dead cells were eliminated from FSC-W vs FSC-H (F2) and SSC-W vs SSC-H (P3), duplicately. Finally, high 7-AAD cells were eliminated, and a living cell gate remained (P4/LIVE). 20,000 P4-gated cells were analyzed. CORIN-positive and PSA-NCAM-positive gates were established, and 0.2% or less cells were retained in Alexa 488-IgG or IgG isotype control secondary antibody.

[Composition of Medium Used in Differentiation Induction of Cells Into Midbrain Dopamine Neuron Cells]

Day 0
8GMK, 10 μM Y-26732 (Wako), 100 nM LDN-193189 (Stemgent), 500 nM A83-01 (Wako)

Day 1-2
8GMK, 100 nM LDN-193189, 500 nM A83-01, 2 μM Purmorphamine (Calbiochem), 100 ng/ml human recombinant FGF-8 (Wako)

Day 37
8GMK, 100 nM LDN-193189, 500 nM A83-01, 2 μM Purmorphamine, 100 ng/ml human recombinant FGF-8, 30 μM CHIR99021 (Stemgent)

Day 7-11
8GMK, 100 nM LDN-193189, 30 μM CHIR99021

On and After Day 12
Neurobasal B27, 200 μM ascorbic acid (Sigma Aldrich), 400 μM dbcAMP (cAMP), 20 ng/ml human recombinant BDNF, 10 ng/ml human recombinant GDNF
8GMK: Glasgow's MEM/8% knockout serum/100 μM sodium pyruvate, 100 μM β-mercaptoethanol
Neurobasal B27: Neurobasal medium/2% B27-added/2 mM Lglutamine

[Transfection]

Before transfection, the cells were subcultured as described above, and the subcultured cells were then seeded at a cell density of 1 to $2 \times 10^5$/well in a differentiation medium comprising a ROCK inhibitor on a 24-well plate coated with iMatrix-511 (E8). On the following day, without replacing the medium with fresh medium, the aforementioned IVT-synthesized mRNA was transfected into the cells by using a StemFect reagent (Stemgent) in accordance with the manufacturer's protocols. For each transfection, 1 μL of the reagent that had been added into 12.5 μl of a StemFect buffer was mixed into a tube (tube A), and the mixture was then incubated at room temperature for 5 minutes. In another tube (tube B), mRNA (up to 400 ng) was mixed with 12.5 μl of a StemFect buffer. The content in the tube B was added dropwise to the tube A for flick-mixing, and the obtained mixture was then incubated at room, temperature for 10 minutes. This transfection complex was added dropwise to the cells, and thereafter, the obtained mixture was stirred and was then placed in an incubator. Four hours later, the old medium containing the transfection complex was aspirated, and a fresh differentiation medium containing no ROCK inhibitors was then added. On the following day, the cells were analyzed according to BD FACS aria-II using a standard filter, or according to FACS analysis by BD Accuri, as described above. The transfection efficiency was evaluated based on mock transfected cells.

[Specific Translational Suppression of 302a-5p- and 367-3p-Responsive hmAG1 mRNAs]

Figure 7:
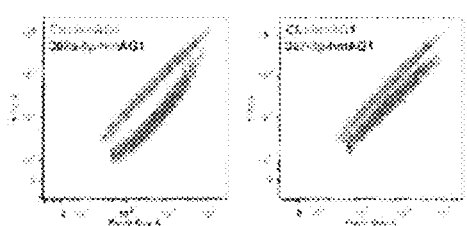
FIG. 7a is a dot plot view showing the results obtained by co-introducing Ctrl-hmAG1, 302a-5p-hmAG1 or 367-3p-hmAG1 into feeder-free human iPS cell lines (201B7, 1231A3, and 1383D7) and HeLa cells, and then analyzing the translation of hmAG1 using BD FACS aria-II.
FIG. 7b is a view showing that the translation of 302a-5p-responsive mRNA and 367-3p-responsive mRNA is specifically suppressed in human iPS cells, and that Hela cells (right-end bar) is constant.
FIG. 7c is a graph showing the ratio of the fluorescence intensity of hmAG1 to the fluorescence intensity of tagBFP, after 302a-5p-responsive mRNA and a 302a-5p inhibitor, the additive amount of which had been changed, were co-introduced into Ff-201B7 (left view), and a dot plot view of cyan, orange, green, blue and red from an inhibitor concentration of 0.003 nM (from the lower side to the upper side of the plot) (right view).
FIG. 7d is a graph showing the ratio of the fluorescence intensity of hmAG1 to the fluorescence intensity of tagBFP, after 302a-5p-responsive mRNA and a 302a-5p mimic, the additive amount of which had been changed, were co-introduced into Hela cells (left view), and a dot plot view of orange, cyan, violet, blue and red from a mimic concentration of 0.003 nM (from the upper side to the lower side of the plot) (right view). The error bar indicates a standard error when trials were repeated three times.
Figure 7:
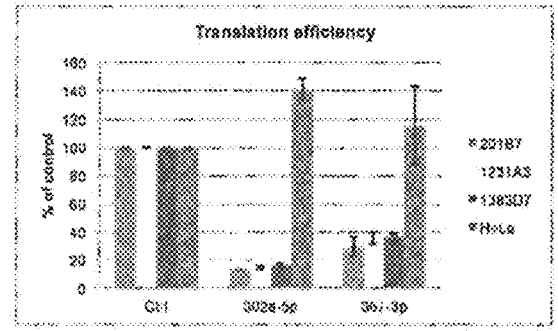
Figure 7:
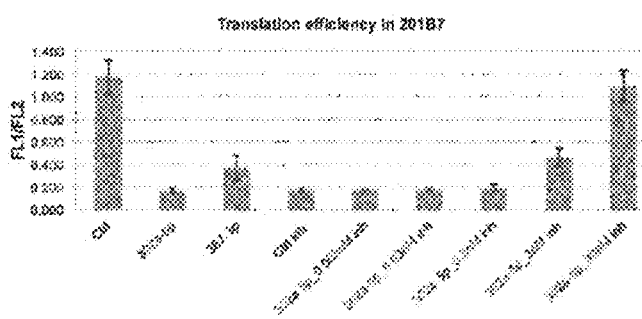
Figure 7:
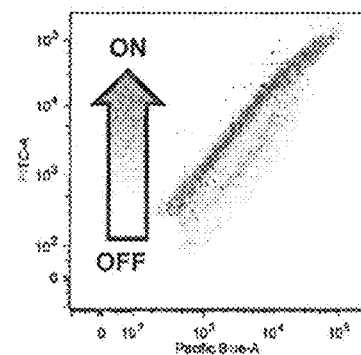
Figure 7:
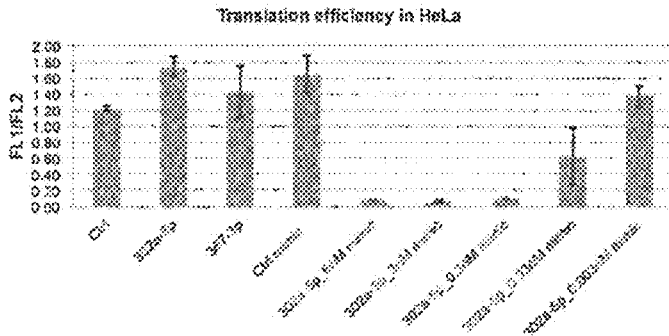
Figure 7:
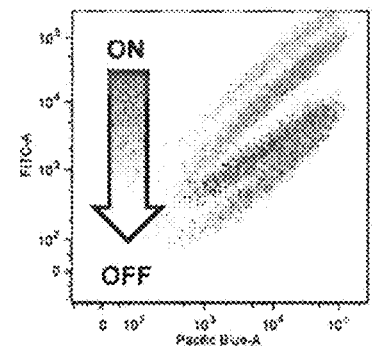

Translation of both 302a-5p- and 367-3p-responsive hmAG1 mRNAs, which had been introduced into human iPS cells, was specifically suppressed (FIG. 7). 50 ng of hmAG1 mRNA (ctrl-hmAG1), 302a-5p-responsive hmAG1 mRNA (302a-5p-hmAG1), or 367-3p-responsive hmAG1 mRNA (3.67-3p-hmAG1) was introduced, together with 100 ng of tagBFP, into feeder-free human iPS cell lines (201B7, 1231A3 and 1383D7) and into HeLa cells. Twenty-four hours later, the cells were harvested, and were then analyzed using BD FACS aria-II. The results are shown in FIG. 7a in the form of a dot plot. Even in the case of using these miRNA-responsive mRNAs, specific translational, suppression in human iPS cells 201B7 was found by a flow cytometric analysis. Moreover, the results from the human iPS cell lines were compared with the results from the HeLa cells. As a result, it was found that the translation of 302a-5p-responsive mRNA and 367-3p-responsive mRNA was specifically suppressed in the human iPS cells, regardless of the cell lines 201B7, 1231A3, and 1383D7 (FIG. 7b). The translation efficiency was calculated by normalizing hmAG1 signals to tagBFP, and it was indicated as a ratio to the cells into which hmAG1 mRNA/tagBFP mRNA had been added.

302a-5p-Responsive mRNA and a 302a-5p inhibitor (whose additive amount was changed) were co-introduced into 201B7 (FIG. 7c). The concentration of the 302a-5p inhibitor was changed in the range from 0.003 nM to 30 nM, and then, it was indicated as dot plots of cyan, orange, green, blue and red from an inhibitor concentration of 0.003 nM (FIG. 7c, right view). When the inhibitor was added in each of concentrations of 3 nM and 30 nM, the two types of inhibitors partially and completely inhibited the translational suppression by 302a-5p-responsive mRNA, respectively. On the other hand, 302a-5p-responsive mRNA and 302a-5p mimic (in different additive amounts) were co-introduced into HeLa cells, which is not responsive to 302a-5p-responsive mRNA (FIG. 7d), The concentration of the 302a-5p mimic was changed in the range, from 0.003 nM to 6 nM, and then, it was indicated as dot plots of orange, cyan, violet, blue and red from a concentration of 0.003 nM (FIG. 7d, right view). These results demonstrated that the 302a-5p mimic inhibits the translation of 302a-5p-responsive mRNA. As described above, 302a-5p-responsive mRNA is specific to target miRNA.

[Differentiation of Ff-Human iPS Cells Into mDA Cells, and Change in Cell Count of miRNA-Responsive Cells]

Figure 8:
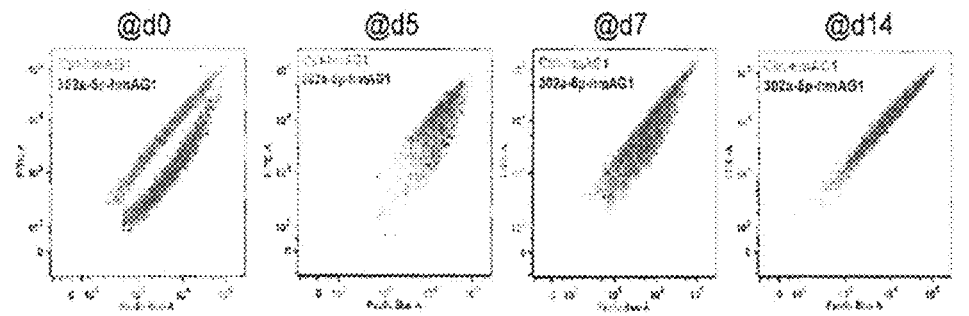
FIG. 8 is a view showing the results obtained by tracking differentiation of Ff-human iPS cells into midbrain dopaminergic cells, using 302a-5p-responsive mRNA and 367-3p-responsive mRNA.
Figure 8:
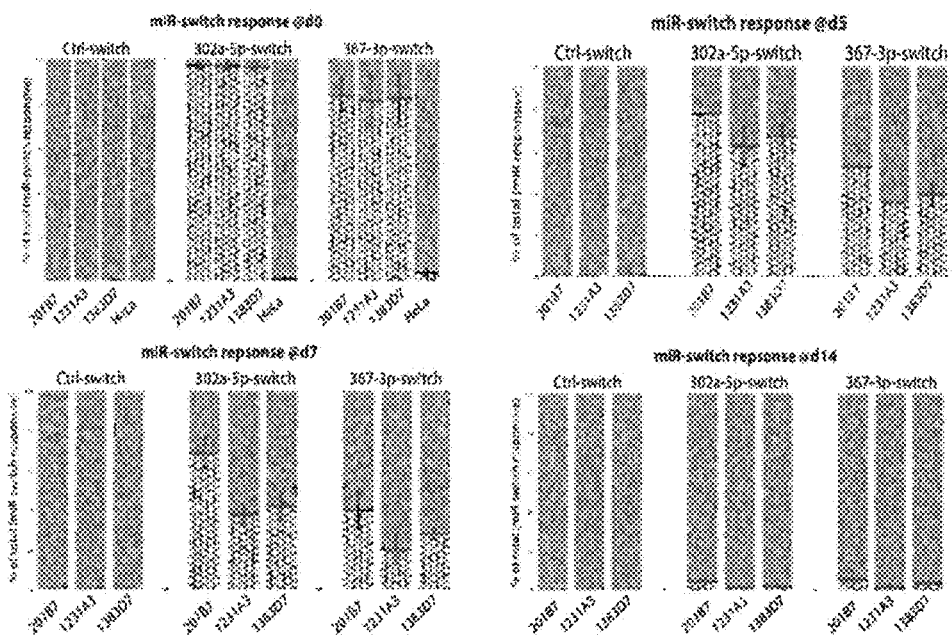
Figure 8:
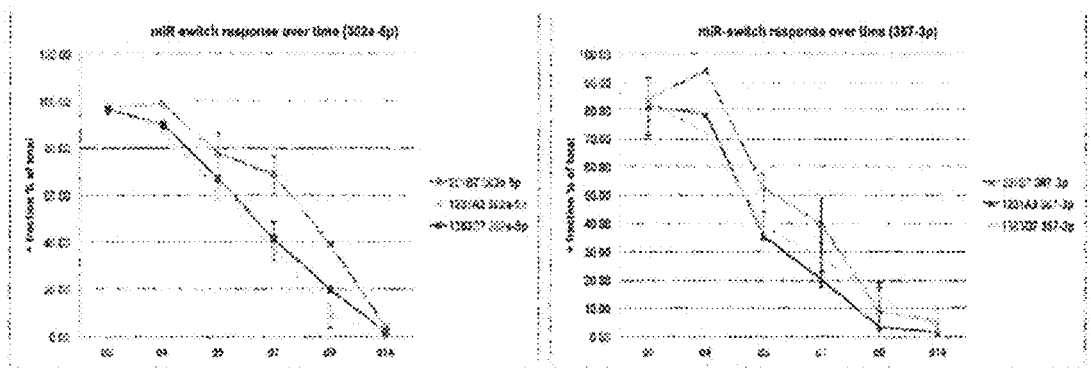

Differentiation of Ff-human iPS cells into midbrain dopaminergic cells (mDA cells) was tracked using 302a-5p-responsive mRNA and 367-3p-responsive mRNA (FIG. 8). From the results obtained by analyzing 302a-5p-responsive mRNA-introduced FT201B7 cells on day 0, day 5, day 7 and day 14 according to flow cytometry, it was demonstrated that, with progression of the differentiation, the translation-suppressing effect of hmAG1 was decreased (FIG. 8a). Moreover, even in a case in which any of 302a-5p-responsive mRNA and 367-3p-responsive mRNA was introduced, the distribution of 302a-5p-responsive cells or 367-3p-responsive cells (blue region) was reduced with progression of the differentiation (FIG. 8b). Furthermore, in all cell lines of Ff-human iPS cells, almost the same results as those described above were confirmed. Further, it was demonstrated that progression of the differentiation can be tracked using 302a-5p-responsive mRNA or 367-3p-responsive mRNA, and that the ease of differentiation is different depending on cell lines.

[Differentiation of Ff-human iPS Cells Into mDA Cells and Quantification of hsa-miR]

Figure 9:
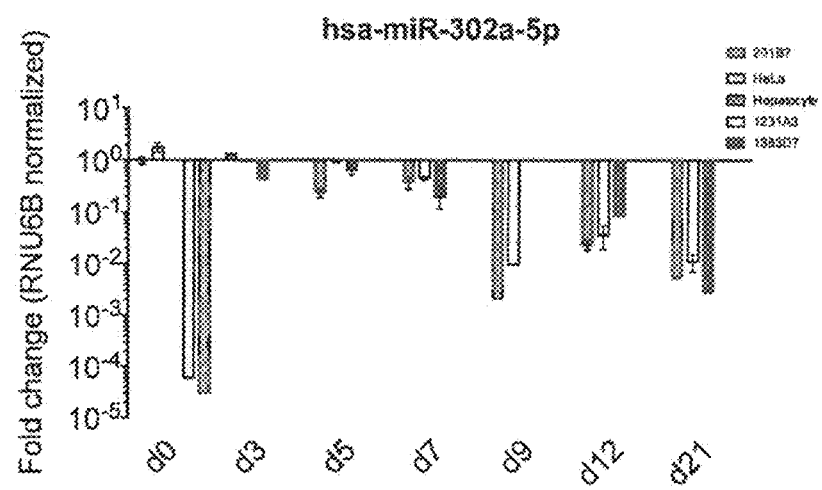
FIG. 9 is a graph showing the ratio between the expression level of hsa-miR-302a-5p (FIG. 9a) and the expression level of hsa-miR-367-3 (FIG. 9b) in individual cells during differentiation from day 0 to day 21 of human iPS cells into mDA cells (midbrain dopamine neuron cells), HeLa cells, and hepatocytes, wherein the ratio has been normalized with RNU6B and has been then shown at a log 10 scale. Both HeLa cells and hepatocytes are used as negative controls in which almost no miRNA has been expressed, and the graph shows that the expression levels of both hsa-miR-302a-5p and hsa-miR-367-3 have been downregulated, as the differentiation from human iPS cells to mDA has progressed. The error bar indicates a standard error when trials were repeated three times.
Figure 9:
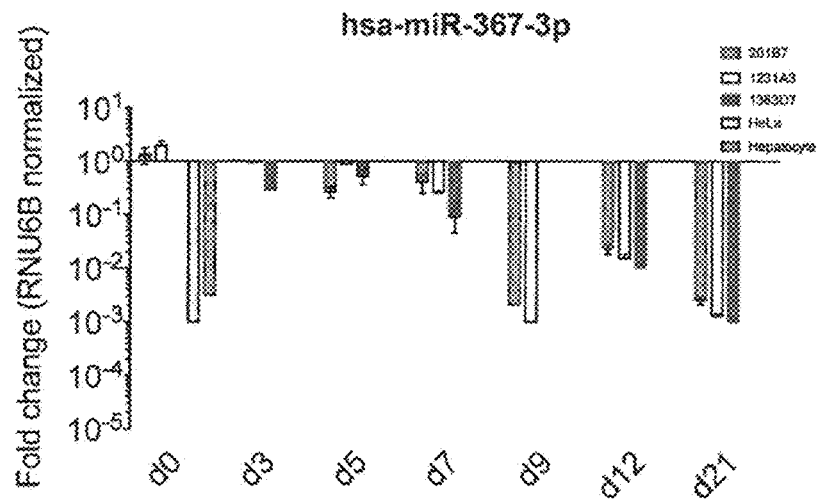

On days 0, 3, 5, 7, 12 and 21 of differentiation of Ff-human iPS cells into mDA cells, total RNA was extracted from frozen cell pellets by triazole extraction and isopropanol precipitation. RNA was treated with DNase, was then reversely transcribed using miRNA reverse transcriptase and target-specific RT primers (Applied Biosystems), and was then amplified using TaqMan miRNA probe. The ratio of hsa-miR302a-5p (FIG. 9a) and that of hsa-miR-367-3p (FIG. 9b) during differentiation, each of which was normalized with RNU6B, are shown at a log 10 scale. HeLa cells and hepatocytes are also shown as negative controls on day 0. It is shown that, during the differentiation of human iPS cells into mDA cells, the expression levels of hsa-miR-302a-5p and hsa-miR-367-3p in individual cells are down-regulated.

[Quantification of Ff-Human iPS Cells in Differentiated Cells]

Figure 10:
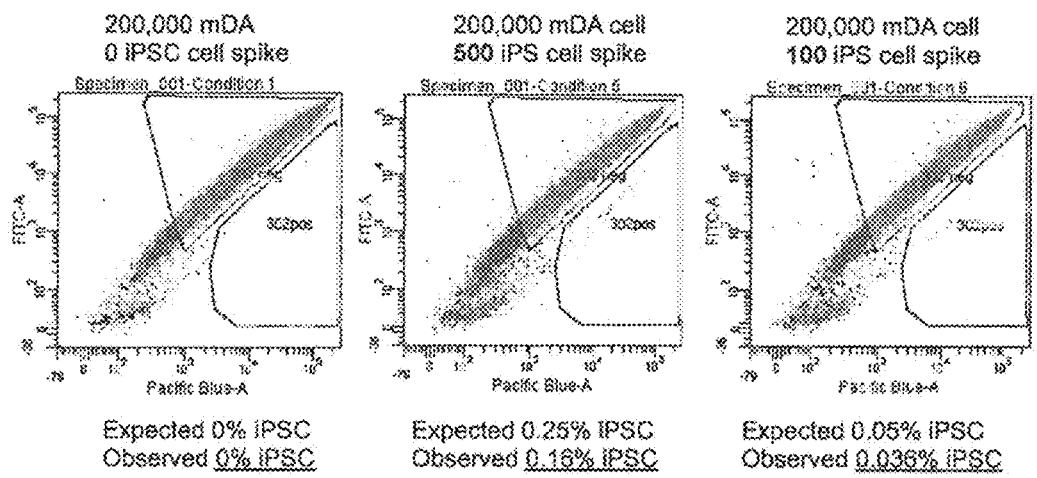
FIG. 10 is a view showing that cells obtained by adding Ff-human iPS cells to a completely differentiated mDA cell line can be detected with high sensitivity. At minimum 100 Ff-201B-7 human iPS cells were added to mDA cells in a 24-well plate. The total cell count was set at 200,000. Into the cells, tagBFP and hmAG1 mRNA or 302a-5p-hmAG1 mRNA were introduced. When 302a-5p-responsive mRNA was introduced into only mDA cells, a 302pos (miR-302a-5p-positive) gate (repeat 1) and a P5 gate (repeat 2) were established. As a result, it was confirmed that there were no miR302a-5p-positive cells (the dot plot in the left-side panel). In the case of both repeat 1 and repeat 2, the measurement value of the ratio of human iPS cells identified by 302a-5p-responsive mRNA to mDA cells was extremely close to the estimated value.
Figure 10:
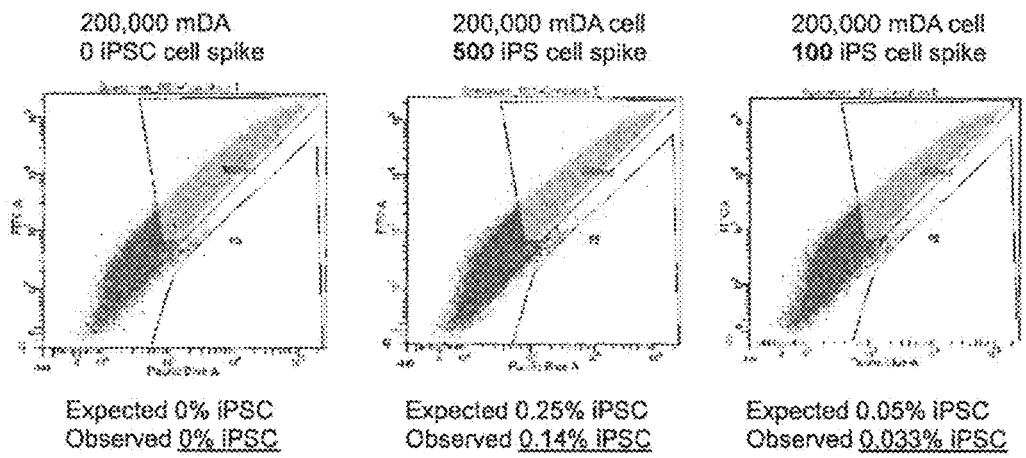

Regarding a completely differentiated mDA cell line, to which a known amount of Ff-human iPS cells had been added, the added amount was measured using miRNA-responsive mRNA (spike test) (FIG. 10). In a 24-well plate, Ff201B7 human iPS cells (cell count: 0, 100, and 500) were added to the mDA cells. The total cell count was set at 200,000. 50 ng of hmAG1 mRNA or 302a-5p-responsive mRNA, and 100 ng of tagBFP were co-introduced into these cells. When 302a-5p-responsive mRNA was introduced into mDA cells that did not contain iPS cells, even though a 302pos (miR-302a-5p-positive) gate (repeat 1) and a P5 gate (repeat 2) were established, cells exhibiting translational suppression were not confirmed (the dot plot in the leftmost panel). As shown in the results of both the repeat 1 and the repeat 2, the measurement value of the ratio of human iPS cells identified by 302a-5p-responsive mRNA to the mDA cells was extremely close to the estimated value thereof.

[Extraction of Differentiated Cells Using miRNA-Responsive puroR mRNA]

Using a puromycin resistance gene as a reporter, an attempt was made to remove the remaining iPS cells from a co-culture system (FIG. 11). FIG. 11a shows a scheme of removing the remaining iPS cells by addition of puromycin. The figure shows that, when 302a-5p-responsive puroR mRNA was introduced into a co-culture line of a 201B7 cell line and mDA cells, not-introduced cells and cells, in which hsa-miR-302a-5p was highly expressed, underwent cell death, since these cells did not have a puromycin resistance gene, or since the expression of the resistance gene was suppressed. FIG. 11b shows an experiment timeline of a single culture system. Herein, $2 \times 10^4$ cells were seeded in a 96-well plate coated with iMatrix-511(E8), In this experimental timeline, Ff-201B7 human iPS cells, and mDA cells that were to be induced, were treated in a medium containing different amounts of puroR mRNA (0 to 50 ng) or puromycin (0 to 10 μg). The results obtained by adding the WST-1 substrate (Roche) for 2 to 4 hours and then assaying cytotoxicity are shown in graphs (the bar graphs of FIG. 11b). In the case of F1-201B7 human iPS cells, when 302a-5p-responsive puroR mRNA (302-PuroR) was introduced into the cells, the ratio of living cells was significantly reduced, when compared with the case of introducing puroR mRNA (Contl-PurpR) that was not responsive to miRNA (FIG. 11b, the leftmost graph and the second graph from the left). In contrast, in the case of mDA cells, even if puroR mRNA (Contl-PurpR) was introduced into the cells, or even if 302a-5p-responsive puroR mRNA was introduced into the cells, almost no change was found, in the ratio of living cells.

A single culture of Ff-201B7 human iPS cells or mDA cells to be induced, or a co-culture thereof was seeded in a 24-well plate, and they were then cultured in a corresponding medium for iPS cells or a corresponding medium for mDA cells, or in a corresponding mixed medium comprising the two types of media (together with a ROCK, inhibitor). On the following day, the medium was exchanged with a medium containing no ROCK inhibitors, and 50 ng of puroR mRNA or 302a-5p-responsive puroR mRNA was then introduced into the cells. Four hours after the expression, the medium was replaced with fresh medium, and 2 μg/ml puromycin was then added thereto. Twenty-hour hours later, the cells were washed with PBS twice, and were then gently stirred, so that the attached remaining cells were harvested. The harvested cells were stained with an Alexa-488-conjugated anti-human TRA-1-60 antibody (BD laboratories). The upper view of FIG. 11c shows the results obtained by measuring with BD Accuri and gating living cells. In the case of a single culture, system of Ff-201B7 human iPS cells, as expected, when 302a-5p-responsive puroR mRNA was introduced into the cells, the histogram of FL-1 (TRA-1-60) was largely reduced with respect to almost all backgrounds, whereas such influence was not observed when puroR mRNA was introduced into the cells. In the histogram obtained from a co-culture system, into which 302a-5p-responsive puroR mRNA had been introduced, a TRA4-60-positive peak was significantly reduced. The lower view shows the absolute number of TRA-1-60-positive cells in all conditions.

[Sequence Listing]

The invention claimed is:

1. A method for extracting differentiated cells from a cell population after induction of the differentiation of pluripotent stem cells, comprising the following steps:
   (1) a step of introducing, into a cell population after induction of the differentiation of pluripotent stem cells, a single stranded mRNA comprising a marker nucleotide sequence operably linked to a target sequence of miRNA specifically and endogenously expressed in pluripotent stem cells, and a poly A tail, wherein the miRNA specifically and endogenously expressed in the pluripotent stem cells is hsa-miR-302 or hsa-miR-367, and wherein the mRNA is introduced into the cell population in a form of a synthetic RNA molecule without using a virus vector construct or DNA vector construct, wherein the target sequence of miRNA is included in a 5' UTR of an open reading frame encoding the marker nucleotide sequence; and
   (2) a step of extracting cells in which the marker nucleotide sequence has been translated.

2. The method according to claim 1, wherein the pluripotent stem cells are human pluripotent stem cells.

3. The method according to claim 1, wherein hsa-miR-302 is hsa-miR-302b, hsa-miR-302a, hsa-miR-302c, or hsa-miR-302d.

4. The method according to claim 1, wherein the step of extracting is carried out using a flow cytometer.

5. The method according to claim 1, wherein the marker nucleotide sequence comprises a nucleotide sequence encoding a drug resistance protein.

6. The method according to claim 1, wherein the mRNA comprises a Cap structure.

7. The method according to claim 1, wherein the target sequence of miRNA is included in a 5' UTR and a 3' UTR of an open reading frame encoding the marker nucleotide sequence.

8. A differentiated cell extraction kit, which comprises a single stranded mRNA comprising a marker nucleotide sequence operably linked to a target sequence of miRNA specifically and endogenously expressed in pluripotent stem cells, and a poly A tail, wherein the miRNA specifically and endogenously expressed in the pluripotent stem cells is hsa-miR-302 or hsa-miR-367, wherein the target sequence of miRNA is included in a 5' UTR of an open reading frame encoding the marker nucleotide sequence.

9. The kit according to claim 8, wherein the pluripotent stem cells are human pluripotent stem cells.

10. The kit according to claim 8, wherein hsa-miR-302 is hsa-miR-302b, hsa-miR-302a, hsa-miR-302c, or hsa-miR-302d.

11. The kit according to claim 8, wherein the marker nucleotide sequence comprises a nucleotide sequence encoding a drug resistance protein.

12. The kit according to claim 8, wherein the mRNA comprises a Cap structure.

13. The kit according to claim 8, wherein the target sequence of miRNA is included in a 5' UTR and a 3' UTR of an open reading frame encoding the marker nucleotide sequence.

* * * * *

UNITED STATES PATENT AND TRADEMARK OFFICE
CERTIFICATE OF CORRECTION

PATENT NO. : 10,604,770 B2
APPLICATION NO. : 15/326083
DATED : March 31, 2020
INVENTOR(S) : Saito et al.

Page 1 of 1

It is certified that error appears in the above-identified patent and that said Letters Patent is hereby corrected as shown below:

In the Specification

Column 5, Line 30: Please correct "254-259:1." to read -- 254-259; --

Column 7, Line 27: Please correct "3-ter-" to read -- 3'-ter- --

Column 8, Line 34: Please correct "3-terminus" to read -- 3'-terminus --

Column 11, Line 50: Please correct "51 UTR" to read -- 5' UTR --

Column 13, Line 39: Please correct "5' UUR" to read -- 5' UTR --

Column 17, Line 62: Please correct "% Glutamax" to read -- 1% Glutamax --

Column 19, Line 21: Please correct "CGCCACCatg" to read -- CGCCACCatg --

Column 20, Line 32: Please correct "tacaattAGATCACA" to read -- tgcaattAGATCACA --

Column 22, Line 12: Please correct "cctttaagtAGATCCA" to read -- cgtttaagtAGATCCA --

Column 23, Line 65: Please correct "hmAG1_ITV" to read -- hmAG1_ITVrev --

Column 25, Line 46: Please correct "(F2)" to read -- (P2) --

Column 26, Line 43: Please correct "(3.67-3p-hmAG1)" to read -- (367-3p-hmAG1) --

Column 27, Line 21: Please correct "FT201B7" to read -- Ff-201B7 --

Column 28, Line 64: Please correct "TRA4-60-" to read -- TRA-1-60- --

Signed and Sealed this
Eighteenth Day of August, 2020

Andrei Iancu
*Director of the United States Patent and Trademark Office*

```
                            SEQUENCE LISTING

<160> NUMBER OF SEQ ID NOS: 33

<210> SEQ ID NO 1
<211> LENGTH: 1019
<212> TYPE: RNA
<213> ORGANISM: Artificial Sequence
<220> FEATURE:
<223> OTHER INFORMATION: reporter

<400> SEQUENCE: 1
gggcgaauua agagagaaaa gaagaguaag aagaaauaua agacaccggu cgccaccaug      60
ggauccguga gcaagggcga ggagcuguuc accggggugg ugcccauccu ggucgagcug     120
gacggcgacg uaaacggcca caaguucagc guguccggcg agggcgaggg cgaugccacc     180
uacggcaagc ugacccugaa guucaucugc accaccggca agcugcccgu gcccuggccc     240
acccucguga ccacccugac cuacggcgug cagugcuuca gccgcuaccc cgaccacaug     300
aagcagcacg acuucuucaa guccgccaug cccgaaggcu acguccagga gcgcaccauc     360
uucuucaagg acgacggcaa cuacaagacc cgcgccgagg ugaaguucga gggcgacacc     420 cugguggaacc gcaucgagcu gaagggcauc gacuucaagg aggacggcaa cauccugggg     480
cacaagcugg aguacaacua caacagccac aacgucuaua ucauggccga caagcagaag     540
aacggcauca ggugaacuu caagauccgc cacaacaucg aggacggcag cgugcagcuc     600
gccgaccacu accagcagaa cacccccauc ggcgacggcc ccgugcugcu gcccgacaac     660
cacuaccuga gcacccaguc cgcccugagc aaagacccca acgagaagcg cgaucacaug     720
guccugcugg aguucgugac cgccgccggg aucacucucg gcauggacga gcuguacaag     780
agaucucaua ugcaucucga gugauagucu agaccuucug cggggcuugc cuucuggcca     840
ugcccuucuu cucccccuug caccuguacc ucuuggucuu ugaauaaagc cugaguagga     900
aaaaaaaaaa aaaaaaaaaa aaaaaaaaaa aaaaaaaaaa aaaaaaaaaa aaaaaaaaaa     960
aaaaaaaaaa aaaaaaaaaa aaaaaaaaaa aaaaaaaaaa aaaaaaaaaa aaaaaaaaa    1019

<210> SEQ ID NO 2
<211> LENGTH: 1018
<212> TYPE: RNA
<213> ORGANISM: Artificial Sequence
<220> FEATURE:
<223> OTHER INFORMATION: reporter

<400> SEQUENCE: 2
ggucagaucc gcuaggaucc uacuaaaaca uggaagcacu acaccgguc gccaccaugg       60 gauccgugag caagggcgag gagcuguuca ccgggguggu gcccauccug gucgagcugg     120
acggcgacgu aaacggccac aaguucagcg uguccggcga gggcgaggggc gaugccaccu     180 acggcaagcu gacccugaag uucaucugca ccaccggcaa gcugcccgug cccuggccca     240
cccucgugac cacccugacc uacggcgugc agugcuucag ccgcuacccc gaccacauga     300
agcagcacga cuucuucaag uccgccaugc ccgaaggcua cguccaggag cgcaccaucu     360
ucuucaagga cgacggcaac uacaagaccc gcgccgaggu gaaguucgag ggcgacaccc     420
uggugaaccg caucgagcug aagggcaucg acuucaagga ggacggcaac auccugggc     480 acaagcugga guacaacuac aacagccaca acgucuauau cauggccgac aagcagaaga     540
acggcaucaa ggugaacuuc aagauccgcc acaacaucga ggacggcagc gugcagcucg     600
ccgaccacua ccagcagaac acccccaucg gcgacggccc cgugcugcug cccgacaacc     660
```

-continued

| | |
|---|---|
| acuaccugag cacccagucc gcccugagca aagaccccaa cgagaagcgc gaucacaugg | 720 |
| uccugcugga guucgugacc gccgccggga ucacucucgg cauggacgag cuguacaaga | 780 |
| gaucucauau gcaucucgag ugauagucua gaccuucugc ggggcuugcc uucuggccau | 840 |
| gcccuucuuc ucucccuugc accuguaccu cuuggucuuu gaauaaagcc ugaguaggaa | 900 |
| aaaaaaaaaa aaaaaaaaaa aaaaaaaaaa aaaaaaaaaa aaaaaaaaaa aaaaaaaaaa | 960 |
| aaaaaaaaaa aaaaaaaaaa aaaaaaaaaa aaaaaaaaaa aaaaaaaaaa aaaaaaa | 1018 |

```
<210> SEQ ID NO 3
<211> LENGTH: 1057
<212> TYPE: RNA
<213> ORGANISM: Artificial Sequence
<220> FEATURE:
<223> OTHER INFORMATION: reporter

<400> SEQUENCE: 3
```

| | |
|---|---|
| gggcgaauua agagagaaaa gaagaguaag aagaaauaua agacaccggu cgccaccaug | 60 |
| ggauccguga gcaagggcga ggagcuguuc accgggguigg ugcccauccu ggucgagcug | 120 |
| gacggcgacg uaaacggcca caaguucagc guguccggcg agggcgaggg cgaugccacc | 180 |
| uacggcaagc ugacccugaa guucaucugc accaccggca agcugcccgu gccuggccc | 240 |
| acccucguga ccacccugac cuacggcgug cagugcuuca gccgcuaccc cgaccacaug | 300 |
| aagcagcacg acuucuucaa guccgccaug cccgaaggcu acguccagga gcgcaccauc | 360 |
| uucuucaagg acgacggcaa cuacaagacc cgcgccgagg ugaaguucga gggcgacacc | 420 |
| cuggugaacc gcaucgagcu gaagggcauc gacuucaagg aggacggcaa cauccugggg | 480 |
| cacaagcugg aguacaacua caacagccac aacgucuaua ucauggccga caagcagaag | 540 |
| aacggcauca aggugaacuu caagauccgc cacaacaucg aggacggcag cgugcagcuc | 600 |
| gccgaccacu accagcagaa caccccauc ggcgacggcc ccgugcugcu gcccgacaac | 660 |
| cacuaccuga gcacccaguc cgcccugagc aaagacccca cgagaagcg cgaucacaug | 720 |
| guccugcugg aguucgugac cgccgccggg aucacucucg gcauggacga gcuguacaag | 780 |
| agaucucaua ugcaucucga gugauagucu agaccuucug cggggccuac uaaaacaugg | 840 |
| aagcacuuac uacuaaaaca uggaagcacu uacuacuaaa acauggaagc acuuacuacu | 900 |
| aaaacaugga agcacuuaug aauaaagccu gaguaggaaa aaaaaaaaa aaaaaaaaa | 960 |
| aaaaaaaaaa aaaaaaaaaa aaaaaaaaaa aaaaaaaaaa aaaaaaaaaa aaaaaaaaaa | 1020 |
| aaaaaaaaaa aaaaaaaaaa aaaaaaaaaa aaaaaaa | 1057 |

```
<210> SEQ ID NO 4
<211> LENGTH: 981
<212> TYPE: RNA
<213> ORGANISM: Artificial Sequence
<220> FEATURE:
<223> OTHER INFORMATION: reporter

<400> SEQUENCE: 4
```

| | |
|---|---|
| gggcgaauua agagagaaaa gaagaguaag aagaaauaua agacaccggu cgccaccaug | 60 |
| gugagcaagg gcgaggagga uaacauggcc aucaucaagg aguucaugcg cuucaaggug | 120 |
| cacauggagg gcuccgugaa cggccacgag uucgagaucg agggcgaggg cgagggccgc | 180 |
| cccuacgagg gcacccagac cgccaagcug aaggugacca agggugggcc ccugcccuuc | 240 |
| gccugggaca uccugucccc ucaguucaug uacggcucca aggccuacgu gaagcacccc | 300 |
| gccgacaucc ccgacuacuu gaagcugucc uuccccgagg cuucaagug ggagcgcgug | 360 |

| | |
|---|---|
| augaacuucg aggacggcgg cguggugacc gugacccagg acuccucccu gcaggacggc | 420 |
| gaguucaucu acaaggugaa gcugcgcggc accaacuucc ccuccgacgg ccccguaaug | 480 |
| cagaagaaga ccaugggcug ggaggccucc uccgagcgga uguacocoga ggacggcgcc | 540 |
| cugaagggcg agaucaagca gaggcugaag cugaaggacg gcggccacua cgacgcugag | 600 |
| gucaagacca ccuacaaggc caagaagccc gugcagcugc ccggcgccua caacgucaac | 660 |
| aucaaguugg acaucaccuc ccacaacgag gacuacacca ucguggaaca guacgaacgc | 720 |
| gccgagggcc gccacuccac cggcggcaug gacgagcugu acaaguaaau cuagaccuuc | 780 |
| ugcggggcuu gccuucuggc caugcccuuc uucucucccu ugcaccugua ccucuugguc | 840 |
| uuugaauaaa gccugaguag gaaaaaaaaa aaaaaaaaaa aaaaaaaaaa aaaaaaaaaa | 900 |
| aaaaaaaaaa aaaaaaaaaa aaaaaaaaaa aaaaaaaaaa aaaaaaaaaa aaaaaaaaaa | 960 |
| aaaaaaaaaa aaaaaaaaaa a | 981 |

<210> SEQ ID NO 5
<211> LENGTH: 35
<212> TYPE: DNA
<213> ORGANISM: Artificial Sequence
<220> FEATURE:
<223> OTHER INFORMATION: primer

<400> SEQUENCE: 5
caccggtcgc caccatggga tccgtgagca agggc                              35

<210> SEQ ID NO 6
<211> LENGTH: 45
<212> TYPE: DNA
<213> ORGANISM: Artificial Sequence
<220> FEATURE:
<223> OTHER INFORMATION: primer

<400> SEQUENCE: 6
gccccgcaga aggtctagac tatcactcga gatgcatatg agatc                   45

<210> SEQ ID NO 7
<211> LENGTH: 38
<212> TYPE: DNA
<213> ORGANISM: Artificial Sequence
<220> FEATURE:
<223> OTHER INFORMATION: primer

<400> SEQUENCE: 7
caccggtcgc caccatggtg agcaagggcg aggaggat                           38

<210> SEQ ID NO 8
<211> LENGTH: 45
<212> TYPE: DNA
<213> ORGANISM: Artificial Sequence
<220> FEATURE:
<223> OTHER INFORMATION: primer

<400> SEQUENCE: 8
gccccgcaga aggtctagat ttacttgtac agctcgtcca tgccg                   45

<210> SEQ ID NO 9
<211> LENGTH: 87
<212> TYPE: DNA
<213> ORGANISM: Artificial Sequence
<220> FEATURE:
<223> OTHER INFORMATION: template

```
<400> SEQUENCE: 9
cagtgaattg taatacgact cactataggg cgaattaaga gagaaaagaa gagtaagaag      60
aaatataaga caccggtcgc caccatg                                          87

<210> SEQ ID NO 10
<211> LENGTH: 28
<212> TYPE: DNA
<213> ORGANISM: Artificial Sequence
<220> FEATURE:
<223> OTHER INFORMATION: primer

<400> SEQUENCE: 10
cagtgaattg taatacgact cactatag                                         28

<210> SEQ ID NO 11
<211> LENGTH: 37
<212> TYPE: DNA
<213> ORGANISM: Artificial Sequence
<220> FEATURE:
<223> OTHER INFORMATION: primer

<400> SEQUENCE: 11
catggtggcg accggtgtct tatatttctt cttactc                               37

<210> SEQ ID NO 12
<211> LENGTH: 92
<212> TYPE: DNA
<213> ORGANISM: Artificial Sequence
<220> FEATURE:
<223> OTHER INFORMATION: template

<400> SEQUENCE: 12
tctagacctt ctgcggggct tgccttctgg ccatgcccct cttctctccc ttgcacctgt      60
acctcttggt ctttgaataa agcctgagta gg                                    92

<210> SEQ ID NO 13
<211> LENGTH: 19
<212> TYPE: DNA
<213> ORGANISM: Artificial Sequence
<220> FEATURE:
<223> OTHER INFORMATION: primer

<400> SEQUENCE: 13
tctagacctt ctgcggggc                                                   19

<210> SEQ ID NO 14
<211> LENGTH: 48
<212> TYPE: DNA
<213> ORGANISM: Artificial Sequence
<220> FEATURE:
<223> OTHER INFORMATION: primer

<400> SEQUENCE: 14
tttttttttt tttttttttt cctactcagg ctttattcaa agaccaag                   48

<210> SEQ ID NO 15
<211> LENGTH: 139
<212> TYPE: DNA
<213> ORGANISM: Artificial Sequence
<220> FEATURE:
<223> OTHER INFORMATION: primer
```

<400> SEQUENCE: 15

```
tttttttttt tttttttttt tttttttttt tttttttttt tttttttttt tttttttttt    60
tttttttttt tttttttttt tttttttttt tttttttttt tttttttttt tttttttttt   120
cctactcagg ctttattca                                                 139
```

<210> SEQ ID NO 16
<211> LENGTH: 68
<212> TYPE: DNA
<213> ORGANISM: Artificial Sequence
<220> FEATURE:
<223> OTHER INFORMATION: primer

<400> SEQUENCE: 16

```
ctcactatag gtcagatccg ctaggatcct actaaaacat ggaagcactt acaccggtcg    60
ccaccatg                                                              68
```

<210> SEQ ID NO 17
<211> LENGTH: 38
<212> TYPE: DNA
<213> ORGANISM: Artificial Sequence
<220> FEATURE:
<223> OTHER INFORMATION: primer

<400> SEQUENCE: 17

```
gctaatacga ctcactatag gtcagatccg ctaggatc                             38
```

<210> SEQ ID NO 18
<211> LENGTH: 148
<212> TYPE: DNA
<213> ORGANISM: Artificial Sequence
<220> FEATURE:
<223> OTHER INFORMATION: primer

<400> SEQUENCE: 18

```
tctagacctt ctgcggggcc tactaaaaca tggaagcact tactactaaa acatggaagc    60
acttactact aaaacatgga agcacttact actaaaacat ggaagcactt atgaataaag   120
cctgagtagg aaaaaaaaaa aaaaaaaa                                       148
```

<210> SEQ ID NO 19
<211> LENGTH: 951
<212> TYPE: DNA
<213> ORGANISM: Artificial Sequence
<220> FEATURE:
<223> OTHER INFORMATION: reporter

<400> SEQUENCE: 19

```
gggcgaatta agagagaaaa gaagagtaag aagaaatata agacaccggt cgccaccatg    60
gtgagcgtga tcaagcccga gatgaagatc aagctgtgca tgagggcac cgtgaacggc   120 cacaacttcg tgatcgaggg cgagggcaag ggcaacccct acgagggcac ccagatcctg   180
gacctgaacg tgaccgaggg cgcccccctg cccttcgcct acgacatcct gaccaccgtg   240
ttccagtacg gcaacagggc cttcaccaag taccccgccg acatccagga ctacttcaag   300
cagaccttcc ccgagggcta ccactgggag aggagcatga cctacgagga ccagggcatc   360
tgcaccgcca ccagcaacat cagcatgagg ggcgactgct tcttctacga catcaggttc   420
gacggcacca acttcccccc caacggcccc gtgatgcaga agaagaccct gaagtgggag   480
cccagcaccg agaagatgta cgtggaggac ggcgtgctga agggcgacgt gaacatgagg   540
ctgctgctgg agggcggcgg ccactacagg tgcgacttca gaccaccta caaggccaag   600
```

```
aaggaggtga ggctgcccga cgcccacaag atcgaccaca ggatcgagat cctgaagcac      660
gacaaggact acaacaaggt gaagctgtac gagaacgccg tggccaggta ctccatgctg      720
cccagccagg ccaagtgaat ctagaccttc tgcggggctt gccttctggc catgcccttc      780
ttctctccct tgcacctgta cctcttggtc tttgaataaa gcctgagtag gaaaaaaaaa      840
aaaaaaaaaa aaaaaaaaaa aaaaaaaaaa aaaaaaaaaa aaaaaaaaaa aaaaaaaaaa      900
aaaaaaaaaa aaaaaaaaaa aaaaaaaaaa aaaaaaaaaa aaaaaaaaaa a              951

<210> SEQ ID NO 20
<211> LENGTH: 956
<212> TYPE: DNA
<213> ORGANISM: Artificial Sequence
<220> FEATURE:
<223> OTHER INFORMATION: reporter

<400> SEQUENCE: 20
ggttccgcga tcgcggatcc agcaagtaca tccacgttta agtagatcca ccggtcgcca       60
ccatggtgag cgtgatcaag cccgagatga agatcaagct gtgcatgagg ggcaccgtga      120
acggccacaa cttcgtgatc gagggcgagg gcaagggcaa ccctacgag ggcacccaga       180 tcctggacct gaacgtgacc gagggcgccc cctgccctt cgcctacgac atcctgacca       240
ccgtgttcca gtacggcaac agggccttca ccaagtaccc cgccgacatc caggactact       300
tcaagcagac cttccccgag ggctaccact gggagaggag catgacctac gaggaccagg      360
gcatctgcac cgccaccagc aacatcagca tgagggggcga ctgcttcttc tacgacatca      420
ggttcgacgg caccaacttc cccccaacg gccccgtgat gcagaagaag accctgaagt      480
gggagcccag caccgagaag atgtacgtgg aggacggcgt gctgaagggc gacgtgaaca      540
tgaggctgct gctggagggc ggcggccact acaggtgcga cttcaagacc acctacaagg      600
ccaagaagga ggtgaggctg cccgacgccc acaagatcga ccacaggatc gagatcctga      660
agcacgacaa ggactacaac aaggtgaagc tgtacgagaa cgccgtggcc aggtactcca      720
tgctgcccag ccaggccaag tgaatctaga ccttctgcgg ggcttgcctt ctggccatgc      780
ccttcttctc tcccttgcac ctgtacctct tggtctttga ataaagcctg agtaggaaaa      840
aaaaaaaaaa aaaaaaaaaa aaaaaaaaaa aaaaaaaaaa aaaaaaaaaa aaaaaaaaaa      900
aaaaaaaaaa aaaaaaaaaa aaaaaaaaaa aaaaaaaaaa aaaaaaaaaa aaaaaa        956

<210> SEQ ID NO 21
<211> LENGTH: 956
<212> TYPE: DNA
<213> ORGANISM: Artificial Sequence
<220> FEATURE:
<223> OTHER INFORMATION: reporter

<400> SEQUENCE: 21
ggttccgcga tcgcggatcc tcaccattgc taaagtgcaa ttagatcaca ccggtcgcca       60
ccatggtgag cgtgatcaag cccgagatga agatcaagct gtgcatgagg ggcaccgtga      120
acggccacaa cttcgtgatc gagggcgagg gcaagggcaa cccctacgag ggcacccaga     180
tcctggacct gaacgtgacc gagggcgccc cctgccctt cgcctacgac atcctgacca       240
ccgtgttcca gtacggcaac agggccttca ccaagtaccc cgccgacatc caggactact      300
tcaagcagac cttccccgag ggctaccact gggagaggag catgacctac gaggaccagg      360
gcatctgcac cgccaccagc aacatcagca tgagggggcga ctgcttcttc tacgacatca     420
ggttcgacgg caccaacttc cccccaacg gccccgtgat gcagaagaag accctgaagt      480
```

| | |
|---|---|
| gggagcccag caccgagaag atgtacgtgg aggacggcgt gctgaagggc gacgtgaaca | 540 |
| tgaggctgct gctggagggc ggcggccact acaggtgcga cttcaagacc acctacaagg | 600 |
| ccaagaagga ggtgaggctg cccgacgccc acaagatcga ccacaggatc gagatcctga | 660 |
| agcacgacaa ggactacaac aaggtgaagc tgtacgagaa cgccgtggcc aggtactcca | 720 |
| tgctgcccag ccaggccaag tgaatctaga ccttctgcgg ggcttgcctt ctggccatgc | 780 |
| ccttcttctc tcccttgcac ctgtacctct tggtctttga ataaagcctg agtaggaaaa | 840 |
| aaaaaaaaaa aaaaaaaaaa aaaaaaaaaa aaaaaaaaaa aaaaaaaaaa aaaaaaaaaa | 900 |
| aaaaaaaaaa aaaaaaaaaa aaaaaaaaaa aaaaaaaaaa aaaaaaaaaa aaaaaa | 956 |

<210> SEQ ID NO 22
<211> LENGTH: 989
<212> TYPE: DNA
<213> ORGANISM: Artificial Sequence
<220> FEATURE:
<223> OTHER INFORMATION: reporter

<400> SEQUENCE: 22

| | |
|---|---|
| gggcgaatta agagagaaaa gaagagtaag aagaaatata agacaccggt cgccaccatg | 60 |
| ggatccagcg agctgattaa ggagaacatg cacatgaagc tgtacatgga gggcaccgtg | 120 |
| gacaaccatc acttcaagtg cacatccgag ggcgaaggca agccctacga gggcacccag | 180 |
| accatgagaa tcaaggtggt cgagggcggc cctctcccct cgccttcga catcctggct | 240 |
| actagcttcc tctacggcag caagaccttc atcaaccaca cccagggcat ccccgacttc | 300 |
| ttcaagcagt cctccctga gggcttcaca tgggagagag tcaccacata cgaagacggg | 360 |
| ggcgtgctga ccgctaccca ggacaccagc ctccaggacg gctgcctcat ctacaacgtc | 420 |
| aagatcagag gggtgaactt cacatccaac ggccctgtga tgcagaagaa aacactcggc | 480 |
| tgggaggcct tcaccgagac gctgtacccc gctgacggcg gcctggaagg cagaaacgac | 540 |
| atggccctga agctcgtggg cgggagccat ctgatcgcaa acatcaagac cacatataga | 600 |
| tccaagaaac ccgctaagaa cctcaagatg cctggcgtct actatgtgga ctacagactg | 660 |
| gaaagaatca aggaggccaa caacgagacc tacgtcgagc agcacgaggt ggcagtggcc | 720 |
| agatactgcg acctccctag caaactgggg cacagatctc atatgcatct cgagtgatct | 780 |
| agaccttctg cggggcttgc cttctggcca tgcccttctt ctctcccttg cacctgtacc | 840 |
| tcttggtctt tgaataaagc ctgagtagga aaaaaaaaaa aaaaaaaaaa aaaaaaaaaa | 900 |
| aaaaaaaaaa aaaaaaaaaa aaaaaaaaaa aaaaaaaaaa aaaaaaaaaa aaaaaaaaaa | 960 |
| aaaaaaaaaa aaaaaaaaa aaaaaaaaa | 989 |

<210> SEQ ID NO 23
<211> LENGTH: 869
<212> TYPE: DNA
<213> ORGANISM: Artificial Sequence
<220> FEATURE:
<223> OTHER INFORMATION: reporter

<400> SEQUENCE: 23

| | |
|---|---|
| gggcgaatta agagagaaaa gaagagtaag aagaaatata agacaccggt cgccaccatg | 60 |
| accgagtaca agcccacggt cgcctcgcc acccgcgacg acgtccccag gccgtacgc | 120 |
| accctcgccg ccgcgttcgc cgactacccc gccacgcgcc acaccgtcga tccggaccgc | 180 |
| cacatcgagc gggtcaccga gctgcaagaa ctcttcctca cgcgcgtcgg gctcgacatc | 240 |
| ggcaaggtgt gggtcgcgga cgacggcgcc gcggtggcgg tctggaccac gccggagagc | 300 |

```
gtcgaagcgg gggcggtgtt cgccgagatc ggcccgcgca tggccgagtt gagcggttcc    360
cggctggccg cgcagcaaca gatggaaggc ctcctggcgc cgcaccggcc caaggagccc    420
gcgtggttcc tggccaccgt cggcgtctcg cccgaccacc agggcaaggg tctgggcagc    480
gccgtcgtgc tccccggagt ggaggcggcc gagcgcgccg gggtgcccgc cttcctggag    540
acctccgcgc ccgcaacct cccccttctac gagcggctcg gcttcaccgt caccgccgac    600
gtcgaggtgc ccgaaggacc gcgcacctgg tgcatgaccc gcaagcccgg tgcctgatct    660
agaccttctg cggggcttgc cttctggcca tgccccttctt ctctcccttg cacctgtacc    720
tcttggtctt tgaataaagc ctgagtagga aaaaaaaaa aaaaaaaaaa aaaaaaaaaa    780
aaaaaaaaaa aaaaaaaaaa aaaaaaaaaa aaaaaaaaaa aaaaaaaaaa aaaaaaaaaa    840
aaaaaaaaaa aaaaaaaaaa aaaaaaaaa                                    869

<210> SEQ ID NO 24
<211> LENGTH: 874
<212> TYPE: DNA
<213> ORGANISM: Artificial Sequence
<220> FEATURE:
<223> OTHER INFORMATION: reporter

<400> SEQUENCE: 24
ggttccgcga tcgcggatcc agcaagtaca tccacgttta agtagatcca ccggtcgcca    60
ccatgaccga gtacaagccc acggtgcgcc tcgccacccg cgacgacgtc cccagggccg    120
tacgcaccct cgccgccgcg ttcgccgact accccgccac gcgccacacc gtcgatccgg    180
accgccacat cgagcgggtc accgagctgc aagaactctt cctcacgcgc gtcgggctcg    240
acatcggcaa ggtgtgggtc gcggacgacg gcgccgcggt ggcggtctgg accacgccgg    300
agagcgtcga agcgggggcg cgtgttcgccg agatcggccc gcgcatggcc gagttgagcg    360
gttcccggct ggccgcgcag caacagatgg aaggcctcct ggcgccgcac cggcccaagg    420
agcccgcgtg gttcctggcc accgtcggcg tctcgcccga ccaccagggc aagggtctgg    480
gcagcgccgt cgtgctcccc ggagtggagg cggccgagcg cgcggggtg cccgccttcc    540 tggagacctc cgcgccccgc aacctcccct tctacgagcg gctcggcttc accgtcaccg    600
ccgacgtcga ggtgcccgaa ggaccgcgca cctggtgcat gacccgcaag cccggtgcct    660
gatctagacc ttctgcgggg cttgccttct ggccatgccc ttcttctctc ccttgcacct    720
gtacctcttg gtctttgaat aaagcctgag taggaaaaaa aaaaaaaaaa aaaaaaaaaa    780
aaaaaaaaaa aaaaaaaaaa aaaaaaaaaa aaaaaaaaaa aaaaaaaaaa aaaaaaaaaa    840
aaaaaaaaaa aaaaaaaaaa aaaaaaaaaa aaaa                              874

<210> SEQ ID NO 25
<211> LENGTH: 36
<212> TYPE: DNA
<213> ORGANISM: Artificial Sequence
<220> FEATURE:
<223> OTHER INFORMATION: primer

<400> SEQUENCE: 25
caccggtcgc caccatggtg agcgtgatca agcccg                              36

<210> SEQ ID NO 26
<211> LENGTH: 39
<212> TYPE: DNA
<213> ORGANISM: Artificial Sequence
<220> FEATURE:
<223> OTHER INFORMATION: primer
```

```
<400> SEQUENCE: 26
gccccgcaga aggtctagat tcacttggcc tggctgggc                                    39

<210> SEQ ID NO 27
<211> LENGTH: 77
<212> TYPE: DNA
<213> ORGANISM: Artificial Sequence
<220> FEATURE:
<223> OTHER INFORMATION: template

<400> SEQUENCE: 27
cgactcacta taggttccgc gatcgcggat ccagcaagta catccacgtt taagtagatc            60
caccggtcgc caccatg                                                            77

<210> SEQ ID NO 28
<211> LENGTH: 77
<212> TYPE: DNA
<213> ORGANISM: Artificial Sequence
<220> FEATURE:
<223> OTHER INFORMATION: template

<400> SEQUENCE: 28
cgactcacta taggttccgc gatcgcggat cctcaccatt gctaaagtgc aattagatca            60
caccggtcgc caccatg                                                            77

<210> SEQ ID NO 29
<211> LENGTH: 39
<212> TYPE: DNA
<213> ORGANISM: Artificial Sequence
<220> FEATURE:
<223> OTHER INFORMATION: primer

<400> SEQUENCE: 29
gctaatacga ctcactatag gttccttaat cgcggatcc                                    39

<210> SEQ ID NO 30
<211> LENGTH: 31
<212> TYPE: DNA
<213> ORGANISM: Artificial Sequence
<220> FEATURE:
<223> OTHER INFORMATION: primer

<400> SEQUENCE: 30
cagtgaattg taatacgact cactataggg c                                            31

<210> SEQ ID NO 31
<211> LENGTH: 35
<212> TYPE: DNA
<213> ORGANISM: Artificial Sequence
<220> FEATURE:
<223> OTHER INFORMATION: primer

<400> SEQUENCE: 31
caccggtcgc caccatgacc gagtacaagc ccacg                                        35

<210> SEQ ID NO 32
<211> LENGTH: 36
<212> TYPE: DNA
<213> ORGANISM: Artificial Sequence
<220> FEATURE:
<223> OTHER INFORMATION: primer

<400> SEQUENCE: 32
gccccgcaga aggtctagat caggcaccgg gcttgc                                       36
```

```
<210> SEQ ID NO 33
<211> LENGTH: 29
<212> TYPE: DNA
<213> ORGANISM: Artificial Sequence
<220> FEATURE:
<223> OTHER INFORMATION: primer

<400> SEQUENCE: 33
caccggtcgc caccatggga tccagcgag                                        29
```